United States Patent [19]
Lazarof

[11] Patent Number: 6,142,782
[45] Date of Patent: *Nov. 7, 2000

[54] IMPLANT ASSEMBLY AND PROCESS FOR PREPARING A PROSTHETIC DEVICE

[76] Inventor: Sargon Lazarof, 21237 Mulholland Dr., Woodland Hills, Calif. 91364

[ * ] Notice: This patent is subject to a terminal disclaimer.

[21] Appl. No.: 09/083,375

[22] Filed: May 22, 1998

Related U.S. Application Data

[60] Continuation-in-part of application No. 08/827,901, Apr. 7, 1997, Pat. No. 5,762,500, which is a division of application No. 08/590,275, Jan. 5, 1996, Pat. No. 5,681,167.

[51] Int. Cl.[7] .................................................. A61C 11/00
[52] U.S. Cl. ........................................... 433/174; 433/213
[58] Field of Search ................................. 433/172, 173, 433/174, 175, 169, 177, 213, 214

[56] References Cited

U.S. PATENT DOCUMENTS

| | | |
|---|---|---|
| 3,708,883 | 1/1973 | Flander . |
| 4,011,602 | 3/1977 | Rybicki et al. . |
| 4,708,654 | 11/1987 | Branemark ............................. 433/213 |
| 4,744,753 | 5/1988 | Ross ....................................... 433/214 |
| 4,850,870 | 7/1989 | Lazzara et al. . |
| 5,004,421 | 4/1991 | Lazarof . |
| 5,022,860 | 6/1991 | Lazzara et al. . |
| 5,087,199 | 2/1992 | Lazarof . |
| 5,192,207 | 3/1993 | Rosellini ............................... 433/218 |
| 5,344,457 | 9/1994 | Pilliar et al. . |
| 5,470,230 | 11/1995 | Daftary et al. . |
| 5,487,663 | 1/1996 | Wilson .................................. 433/218 |
| 5,489,210 | 2/1996 | Hanosh . |
| 5,513,989 | 5/1996 | Crisio . |
| 5,538,426 | 7/1996 | Harding et al. ....................... 433/214 |
| 5,564,921 | 10/1996 | Marlin . |
| 5,564,924 | 10/1996 | Kwan . |
| 5,658,147 | 8/1997 | Phimmasone ......................... 433/213 |
| 5,662,476 | 9/1997 | Ingber et al. .......................... 433/213 |
| 5,681,167 | 10/1997 | Lazarof . |
| 5,685,715 | 11/1997 | Beaty et al. ........................... 433/214 |
| 5,688,123 | 11/1997 | Meiers et al. ......................... 433/214 |
| 5,762,500 | 6/1998 | Lazarof ................................. 433/213 |
| 5,904,483 | 5/1999 | Wade ..................................... 433/214 |

OTHER PUBLICATIONS

Aticle obtained from a Dental School Journal dated in 1969 and a translation, 2 pages.

*Primary Examiner*—Ralph A. Lewis
*Attorney, Agent, or Firm*—Kelly Bauersfeld Lowry & Kelley, LLP

[57] ABSTRACT

An implant assembly includes an elongated hollow body having a skirt which can be positively secured within a bore in a bone of a patient by an expander mechanism, and an abutment which extends from the skirt outwardly from the bore for supporting a prosthetic component. Optionally, an abutment post may be provided which has a head position adjacent to the abutment and a shank received within the hollow body. In a related process for preparing the prosthesis, a transfer component is utilized to replicate the body portion surrounding the implant to facilitate manufacturing the prosthetic component. In this regard, an impression is taken over the abutment with the associated transfer component, and an implant analog having the transfer component associated therewith is inserted into the impression. A stone mold is created utilizing the impression having the inserted implant analog, which stone mold is utilized to form the prosthesis.

55 Claims, 18 Drawing Sheets

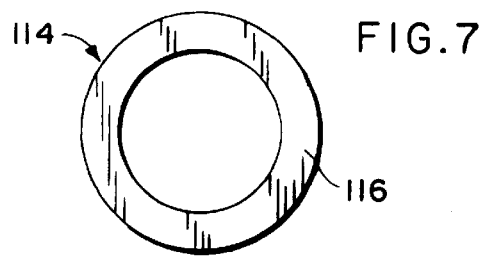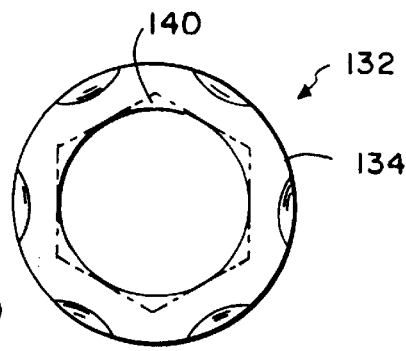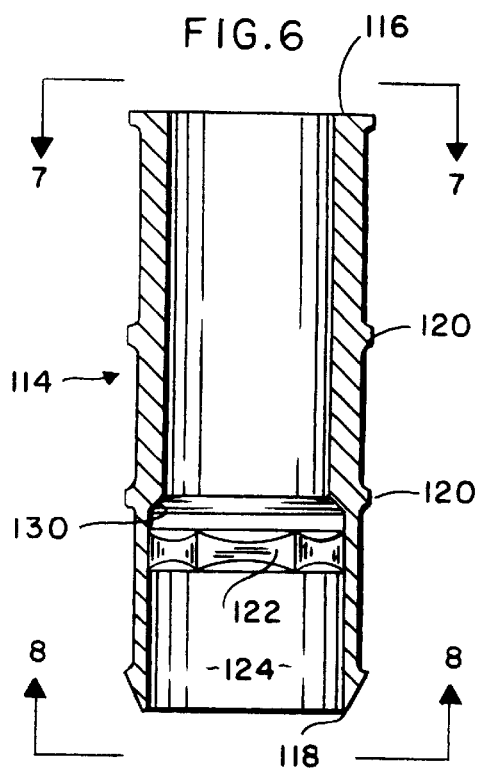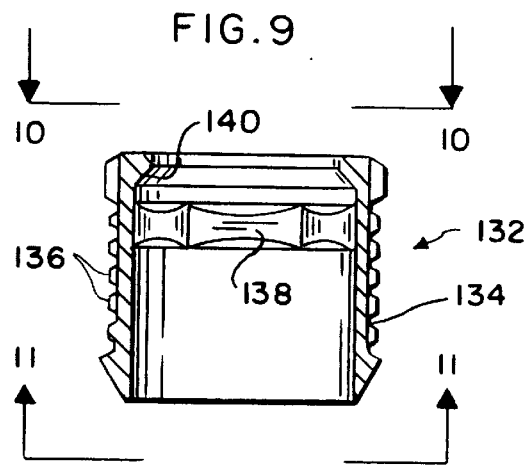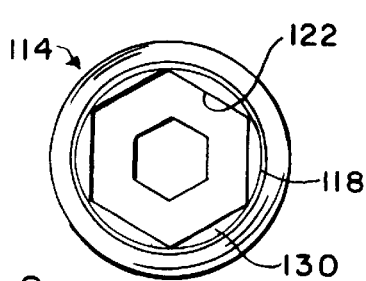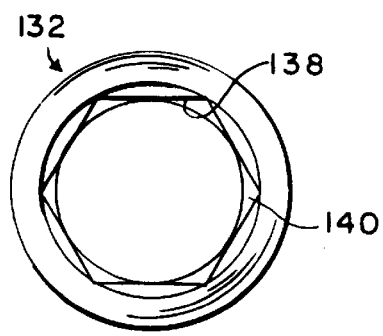

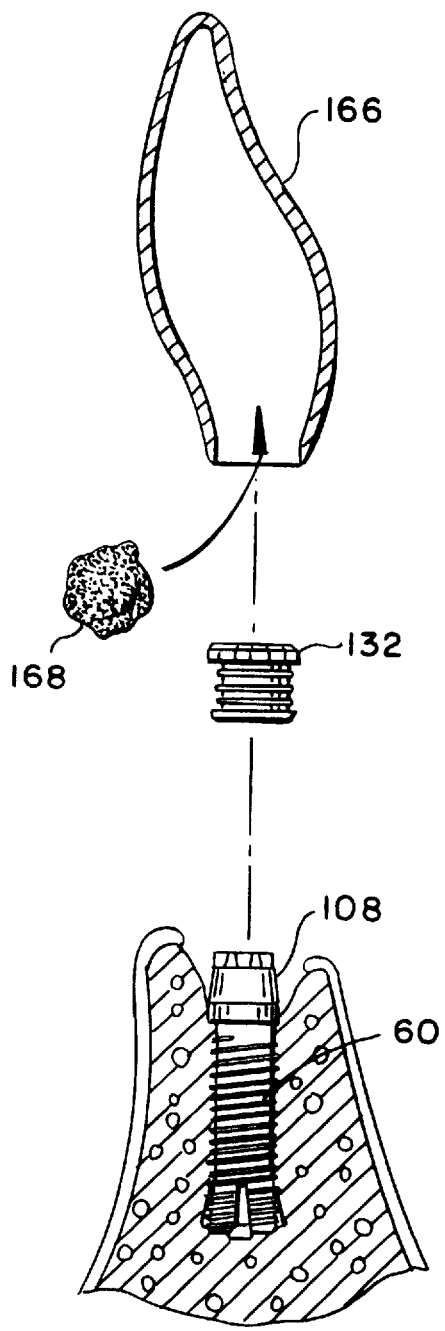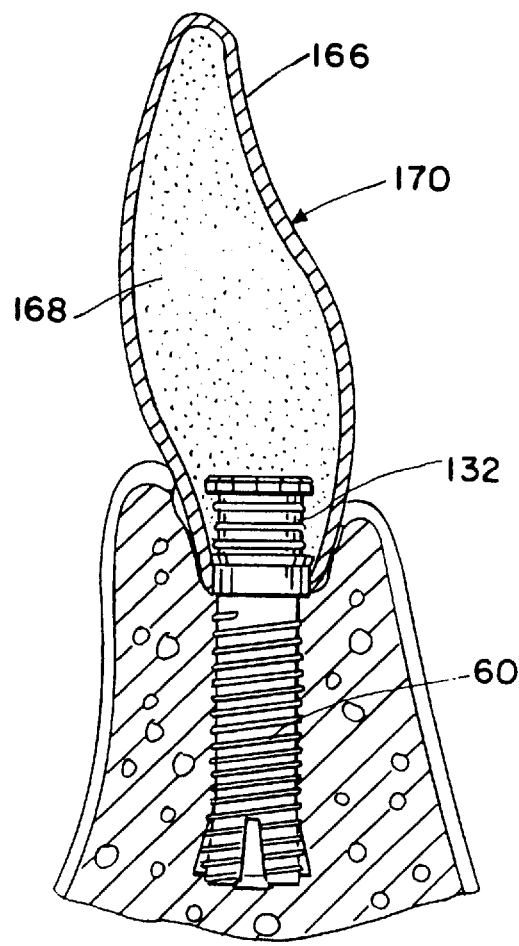
FIG. 22
FIG. 23

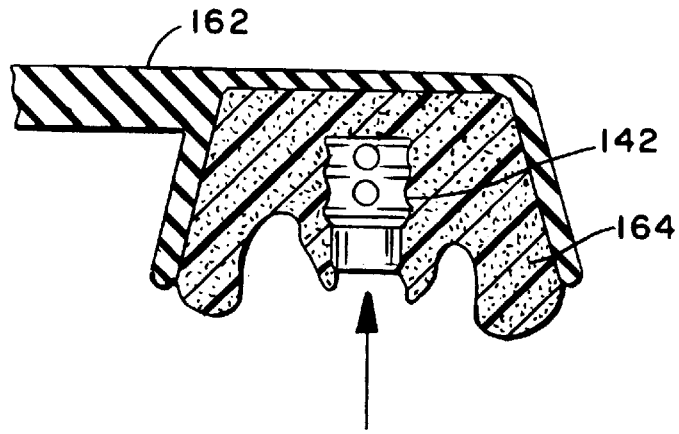
FIG. 24
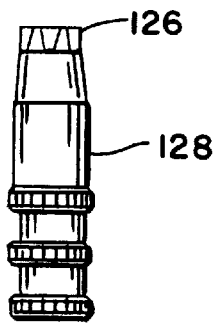
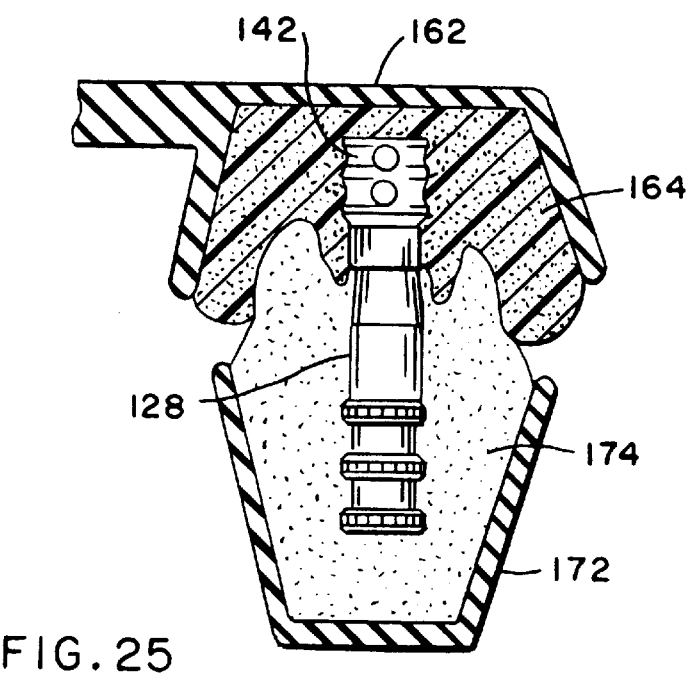
FIG. 25

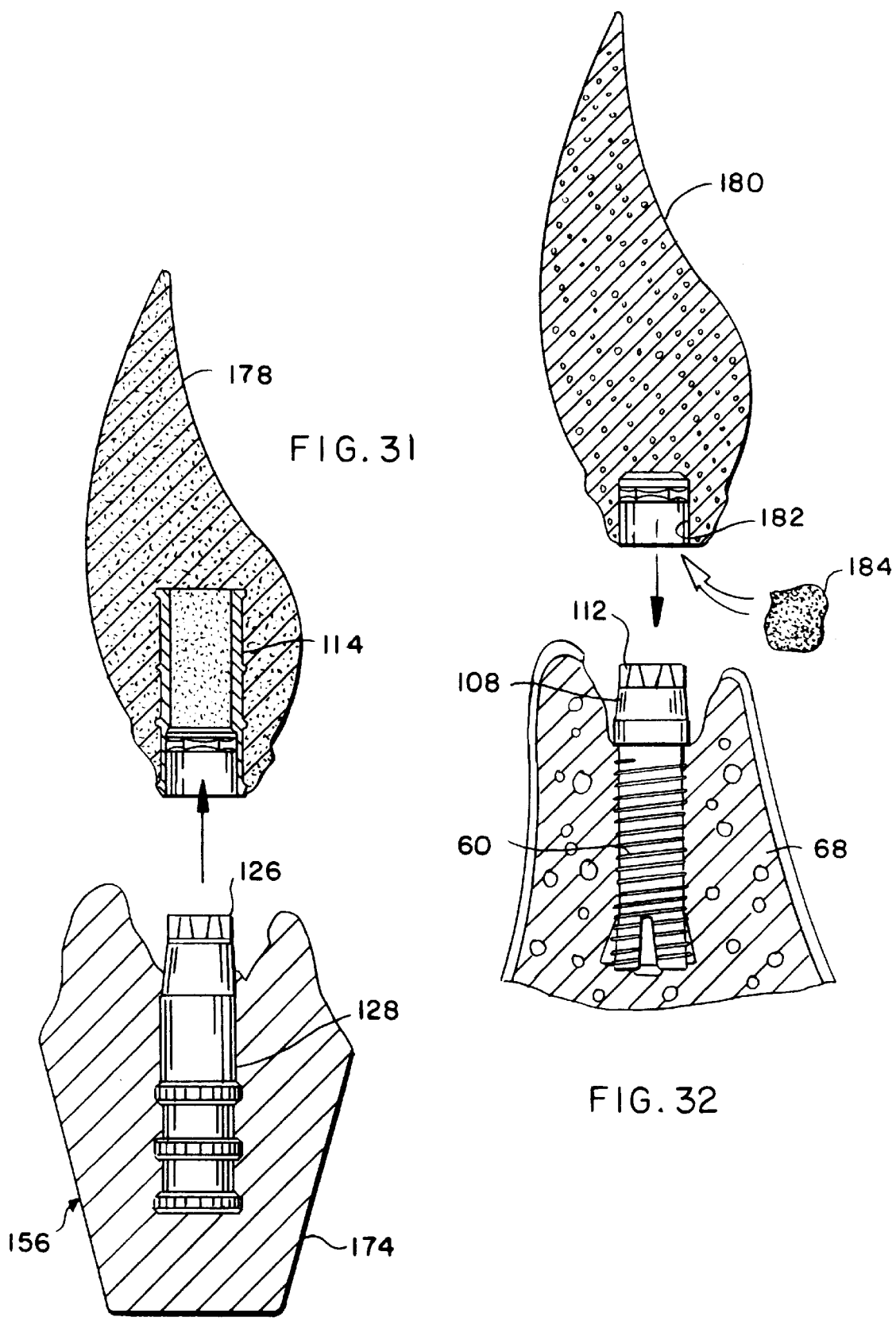

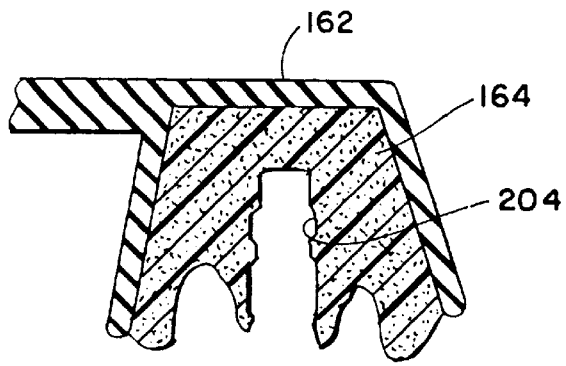
FIG. 40
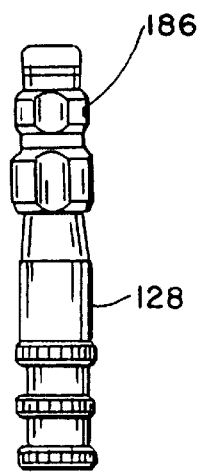
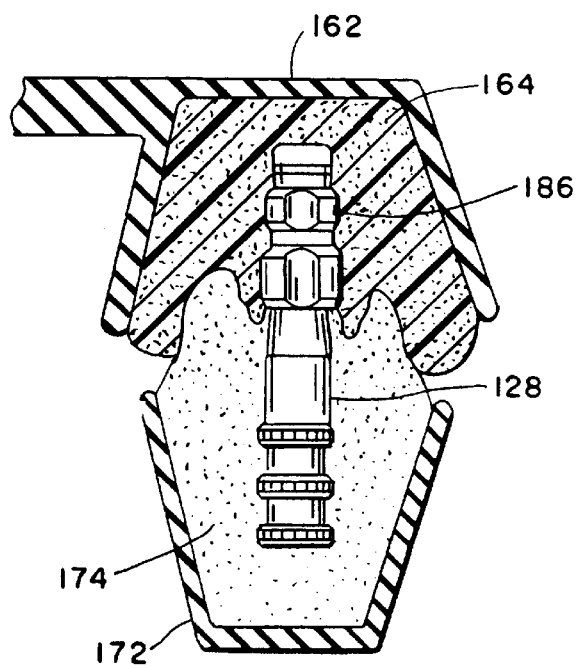
FIG. 41

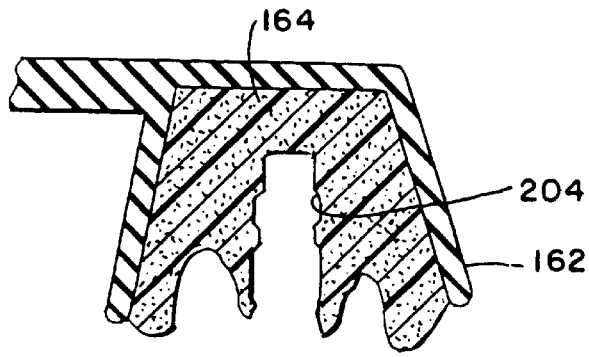
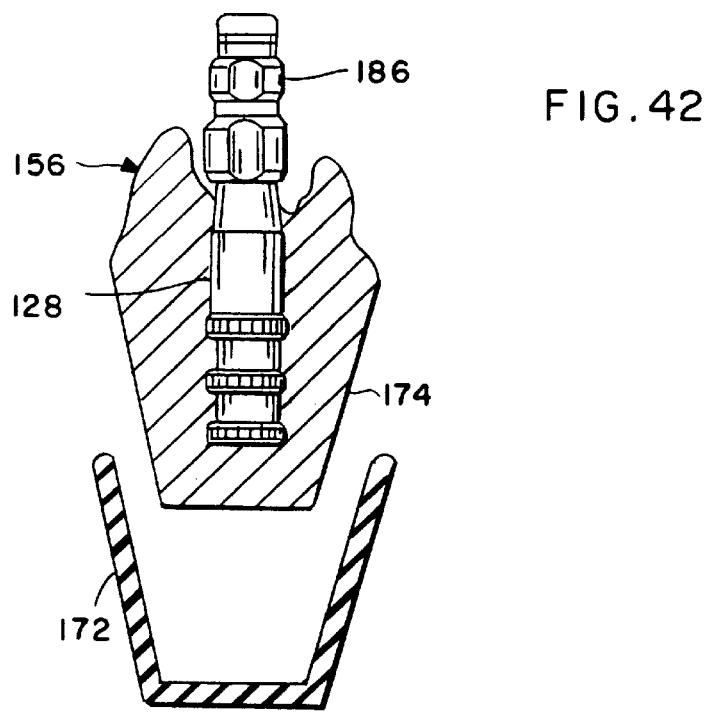
FIG. 42
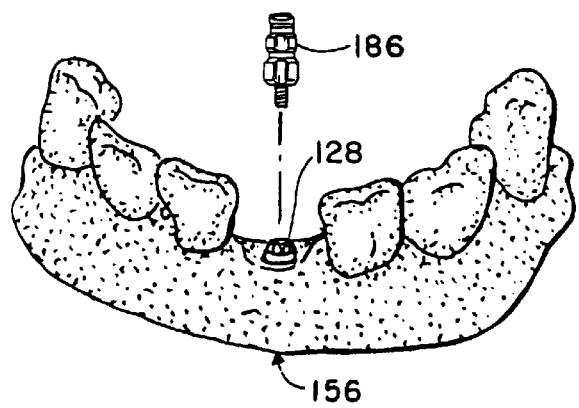
FIG. 43

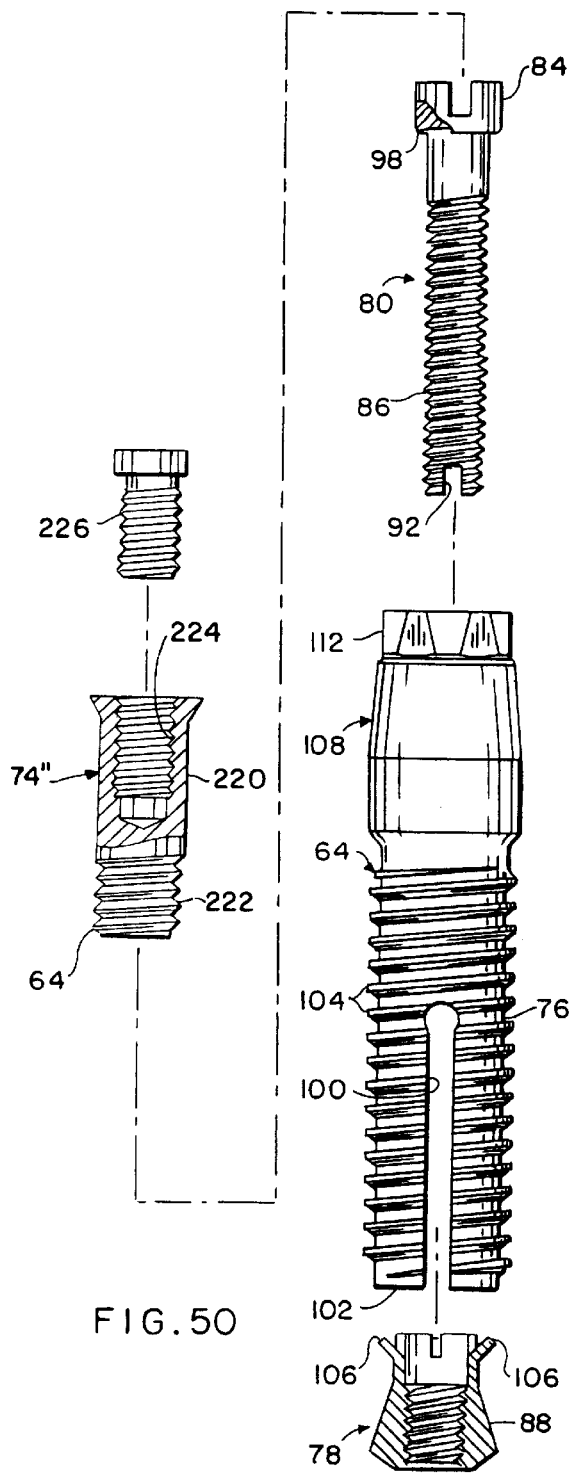
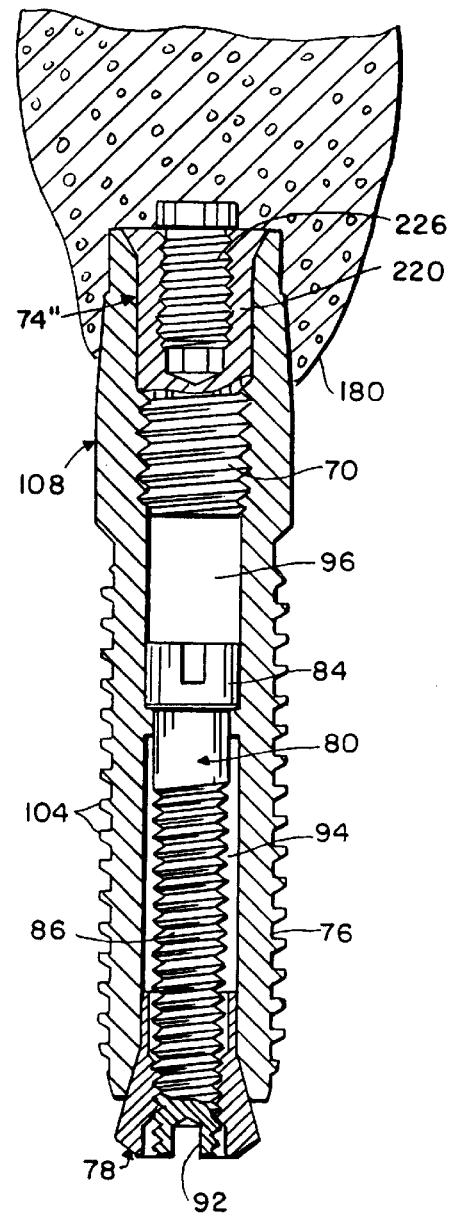
FIG. 50
FIG. 51

IMPLANT ASSEMBLY AND PROCESS FOR PREPARING A PROSTHETIC DEVICE

RELATED APPLICATION

This application is a continuation-in-part of U.S. patent application Ser. No. 08/827,901, filed Apr. 7, 1997, entitled PROCESS FOR PREPARING A TOOTH PROSTHESIS FOR ATTACHMENT TO AN ABUTMENT WITHIN A MOUTH OF A PATIENT now U.S. Pat. No. 5,762,500, which is a division of U.S. application Ser. No. 08/590,275, filed Jan. 5, 1996, entitled DENTAL ASSEMBLY AND PROCESS FOR PREPARING A TOOTH PROSTHESIS, now U.S. Pat. No. 5,681,167.

BACKGROUND OF THE INVENTION

The present invention relates generally to medical/dental prosthetics and processes for preparing such prosthetics, including tooth prostheses. More particularly, the present invention concerns an implant assembly which includes a tubular body portion that can be positively secured within a bore in a bone by an expander mechanism, and a unique transfer technique for preparing a prosthetic device.

Dental implants of the character receivable within a bore provided in the jawbone are old in the art. Typically such implants comprise an apertured body portion which is emplaced within a bore drilled in the bone. The body portion is designed so that during a period of about four to six months after its emplacement within the bore, bone tissue will grow into the aperture so as to secure the body portion of the implant in place within the bone bore. Following this four to six month period, an artificial tooth or other prosthetic component is secured to the body portion.

The procedure is undesirable in several respects. In the first place, the procedure is protracted and requires multiple visits to the oral surgeon. Secondly, during the extended period of time required for the bone tissue to grow into and around the implant, the patient is left with an uncomfortable and unsightly cavity where the prosthetic component, such as an artificial tooth, will eventually go. Additionally, this procedure does not always provide adequate anchoring of the implant to the jawbone so that in time the implant can loosen.

In order to overcome the drawbacks of the standard procedure described above, several types of implants using mechanical locking means for securing the implant in place within the bore in the jawbone have been suggested. Exemplary of such devices is the device described in U.S. Pat. No. 3,708,883 issued to Flander. An improved dental implant is illustrated and described in U.S. Pat. Nos. 5,004,421 and 5,807,199 issued to Lazarof. The Lazarof dental implant makes use of mechanical securement means, but unlike the Flander device, the Lazarof device includes means by which selected dental prosthetics of standard design can be threadably interconnected. In this way, angular corrections of the prosthetic, such as an artificial tooth, can readily be made. Further, in one form, the Lazarof implant is positively secured within the bore in the bone by two separate but cooperating securement mechanisms. The first securement mechanism comprises self-tapping, external threads provided on the tubular body of the device which are threaded into the bone by rotating the device in a first direction. The second cooperating securement mechanism comprises a plurality of bone penetrating anchor blades formed on the skirt portion of the tubular body which are moved into a bone engagement position only after the implant has been securely threaded into the bone. The anchor blades are moved into the bone engagement configuration by rotating a threaded expander member also in a first direction. However, because the threads on the expander member are opposite to the threads on the tubular body, rotational forces exerted on the expander member continuously urge the implant in a tightening direction. In other words, as the anchor blades are urged outwardly, the implant is continuously urged into threaded engagement with the bone. This double locking approach permits the selected prosthetic component to be connected to the implant immediately without the patient having to return to the oral surgeon a second time.

Often an abutment over which a tooth prosthesis is formed, is fixed to an exposed end of the dental implant. Typically, the prior abutments either accommodated a bolt which passed longitudinally through an open central bore for securing the abutment to the implant, or were provided an integral threaded shaft to permit the abutment to be screwed directly into the implant. Such abutment to implant attachment has not been entirely satisfactory, however, since it is very undesirable that any relative movement between the abutment and the implant be permitted once brought together, and particularly after a prosthesis has been attached to the abutment. Without actually cementing the abutment to the implant, there always exists the possibility that the abutment will loosen, resulting in undesirable rotation of the dental prosthesis.

Since dental prosthetic devices are typically manufactured in a laboratory, a major concern of dentists and laboratory technicians is the accurate transfer of information from the patient/dentist to the lab. Such information includes the size and shape of adjacent teeth, the position of the implant and the precise configuration of the abutment, since it is often shaped by the dentist in preparation.

Accordingly, there has been a need for an improved prosthetic implant assembly which is of simplified construction and which incorporates advantages over the prior art. Further, there exists a need for a novel process for preparing a prosthetic device. The present invention fulfills these needs and provides other related advantages.

SUMMARY OF THE INVENTION

The present invention resides in a novel implant assembly and a related process for preparing a prosthetic device. Although the following description of the invention relates specifically to a novel dental assembly and process for preparing a tooth prosthesis, the invention may be applied to the manufacture of other medical prosthetic devices as well. More particularly, the implant assembly comprises, generally, an elongated hollow body including a skirt receivable within a bore provided in a bone of a patient, an internal shoulder, and an abutment which extends from the skirt outwardly from the bore for supporting a prosthetic component. The skit is radially movable within the bore from a first retracted position to a second expanded position. Means are further provided for causing the radial movement of the skirt from the first retracted position to the second expanded position. Optionally, an abutment post may be provided which has a head positioned adjacent to the abutment and a shank received within the hollow body.

In one preferred form of the invention, the means for causing radial movement of the skirt from the first retracted position to the second expanded position includes a draw screw and an expansion nut mechanism. The draw screw has a head which is captured within the hollow body, and a threaded shank which is connected to the head and extends to an end of the skirt. The draw screw head engages the internal shoulder of the elongated hollow body to form a seal which isolates a first hollow body chamber on one side of the draw screw head from a second hollow body chamber on an opposite side thereof. The expansion nut has a skirt-engaging side wall and an inner threaded cavity into which the shank of the draw screw is threaded. Rotation of the draw screw through the inner cavity of the expansion nut causes radial movement of the skirt from the first retracted position to the second expanded position. The skit includes an inclined internal surface, and the expansion nut comprises a skit engaging portion having an inclined external surface. The inclined external surface of the expansion nut is movable into engagement with the inclined internal surface of the skirt upon rotation of the draw screw through the inner cavity of the expansion nut. In order to prevent withdrawal of the threaded shank from the expansion nut, an end of the draw screw threaded shank opposite the draw screw head is enlarged.

The skirt further comprises at least two anchor segments defined by a plurality of circumferentially spaced, longitudinally extending slits, which anchor segments are moveable from the first retracted position to the second expanded position. The anchor segments include bone penetrating means for penetrating the bone of the patient upon movement of the segments into the second expanded position. The expansion nut includes a plurality of tabs which are configured for alignment with the longitudinally extending slits. Placement of the tabs within the longitudinally extending slits prevents rotation of the expansion nut as the draw screw is turned therein.

The abutment includes at least one radially outwardly facing planar surface that may be engaged by the prosthetic component to prevent relative rotation therebetween. The abutment further includes a ring having a diameter larger than the bone, which provides a shoulder facing the bore. The at least one radially outwardly facing planar surface of the abutment in shown, in the preferred embodiments, as an upper hexed collar, which presents a plurality of radially outwardly facing planar surfaces.

In one form of the invention, the optional abutment post includes an O-ring encircling a portion of the abutment post shank. In this particular embodiment, the abutment post shank is press-fit into the hollow body. In another form, abutment post shank is threadably received within the hollow body. In this case, the abutment post head includes an internally threaded, externally accessible cavity which is capable of threadably receiving a screw. In yet another form of the invention, the abutment post head includes a threaded aperture therethrough which has an axis that is inclined relative to the longitudinal axis of the abutment post head. The threaded aperture has an externally accessible first open end and a second open end positioned adjacent to the abutment.

The prosthetic device may be press-fit, screw-retained or cement-retained to the abutment, depending on the needs of the patient and the preferences of the medical practitioner.

In accordance with a process for preparing a prosthesis for attachment to an abutment anchored to a bone of a patient, a transfer component is first associated with the abutment, and then an impression is taken over the abutment with the associated transfer component. An implant analog having the transfer component associated therewith is inserted into the impression, and a stone mold is created utilizing the impression having the inserted implant analog. The stone mold is then utilized to form the prosthesis which, when completed, may be affixed to the bone-anchored abutment.

More particularly in connection with one preferred process embodying the invention, a transfer sleeve is placed over the abutment prior to taking the impression. As the impression is taken, the transfer sleeve is transferred to the impression. An implant analog is then placed into the impression through the transfer sleeve, and a stone mold is created utilizing the impression having the inserted implant analog.

In another preferred process embodying the invention, an impression post assembly is attached to the abutment such that a portion thereof overlies the abutment. An impression is taken over the abutment with the associated impression post assembly. Next, the impression post assembly is removed from the abutment and attached in a like manner to an implant analog. The implant analog having the attached impression post assembly is then inserted into the impression. A stone mold of the body portion of the patient surrounding the abutment may then be created utilizing the impression of the body portion of the patient surrounding the abutment having the attached impression post assembly. The impression post assembly is then removed from the implant analog prior to utilizing the stone mold to form the prosthesis.

In both preferred processes, utilization of the stone mold to form the prosthesis includes the steps of placing a waxing sleeve over the implant analog which extends from the stone mold. The waxing sleeve is filled with wax and a wax-up of a prosthetic component to be formed over the waxing sleeve is prepared. The wax-up and the waxing sleeve are removed from the stone mold and are subsequently invested in another stone mold. The prosthesis is then cast from the stone mold formed from the wax-up and the waxing sleeve.

The prosthesis may be attached to the abutment utilizing an adhesive (cement-retained), or it may be mechanically attached to the abutment (press-fit or screw-retained).

Once the impression has been taken, a provisional prosthetic component may be secured to the abutment while the final prosthesis is being manufactured. In the case of a dental implant, a provisional tooth may be secured in place over the abutment utilizing the steps of placing the treatment crown sleeve over the abutment, filling a denture tooth with a composite material, and placing the composite filled denture tooth over the treatment crown sleeve.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 6 is an elevational sectional view of a waxing sleeve, the use of which is more fully explained in connection with the discussion of FIGS. 28–31;

FIG. 7 is a top plan view of the waxing sleeve taken generally along the line 7—7 of FIG. 6;

FIG. 8 is a bottom plan view of the waxing sleeve taken generally along the line 8—8 of FIG. 6;

FIG. 9 is an elevational sectional view of a treatment crown sleeve, the use of which is more fully described in connection with the discussion of FIGS. 22 and 23;

FIG. 10 is a top plan view of the treatment crown sleeve taken generally along the line 10—10 of FIG. 9;

FIG. 11 is a bottom plan view of the treatment crown sleeve taken generally along the line 11—11 of FIG. 9;

FIGS. 18–32 illustrate steps involved in one illustrated process for preparing a prosthetic device in accordance with the present invention, wherein:

FIG. 18 is a cross-sectional view of a jawbone illustrating the implant assembly positioned therein;

FIG. 19 illustrates the step of placing the transfer sleeve over the abutment portion of the implant assembly;

FIG. 20 illustrates the step of taking an impression of the mouth over the abutment and the transfer sleeve;

FIG. 21 illustrates the step of removing the transfer sleeve with the impression material;

FIG. 22 illustrates the step of placing the treatment crown sleeve of FIG. 9 over the abutment and filling a provisional (temporary tooth) with a composite material;

FIG. 23 illustrates placing the composite filled provisional over the abutment and the treatment crown sleeve as an interim step to provide a temporary tooth prosthesis while the permanent crown is being manufactured in the laboratory;

FIG. 24 illustrates the step of inserting the implant analog into the transfer sleeve embedded in the impression of the mouth;

FIG. 25 illustrates the step of making a stone cast of the mouth over the implant analog;

FIG. 26 illustrates the step of removing the cast and the mouth impression from the stone mold; FIG. 27 is a perspective view illustrating the stone mold having the implant analog embedded therein;

FIG. 28 illustrates the step of placing a waxing sleeve over the implant analog extending from the stone mold;

FIG. 29 illustrates the step of filling the waxing sleeve with a wax;

FIG. 30 illustrates the step of forming a wax-up of the tooth prosthesis;

FIG. 31 illustrates the step of removing the wax-up for purposes of forming a crown utilizing standard casting procedures; and FIG. 32 illustrates the step of fixing the final crown having an internal cavity precisely matching the external configuration of the abutment, to the implant assembly within the patient's mouth;

FIGS. 33–43 illustrate use of an impression post assembly in another illustrated process for preparing a prosthetic device in accordance with the present invention, wherein:

FIG. 33 is an elevational view of an impression post assembly;

FIG. 34 illustrates the step of attaching the impression post assembly to the abutment portion of the implant assembly;

FIG. 35 illustrates the step of taking an impression of the mouth over the abutment and the attached impression post assembly;

FIG. 36 illustrates the step of removing the impression material;

FIG. 37 illustrates the step of removing the impression post assembly from the implant assembly;

FIG. 38 is an elevational view illustrating attachment of the impression post assembly to an implant analog;

FIG. 39 is an enlarged sectional view taken generally along the line 39—39 of FIG. 38;

FIG. 40 illustrates the step of inserting the implant analog having the attached impression post assembly into the impression of the mouth;

FIG. 41 illustrates the step of making a stone cast of the mouth over the implant analog;

FIG. 42 illustrates the step of removing the cast and the mouth impression from the stone mold; and FIG. 43 is a perspective view illustrating the stone mold having the implant analog embedded therein, and further illustrating removal of the impression post assembly from the implant analog, wherein the remaining steps of manufacturing and installing a prosthetic device follow those illustrated in FIGS. 28–32 described above;

FIG. 50 is an exploded elevational and partially sectional view of another implant assembly embodying the present invention, wherein the abutment post comprises a plug threadably received within the elongated hollow body, which plug itself is threaded to receive a screw that may be fixed to a prosthetic component; and FIG. 51 is an elevational section of the components illustrated in FIG. 50, illustrating screw retention of a prosthetic component to the implant assembly.

DETAILED DESCRIPTION OF THE PREFERRED EMBODIMENTS

Figure 1:
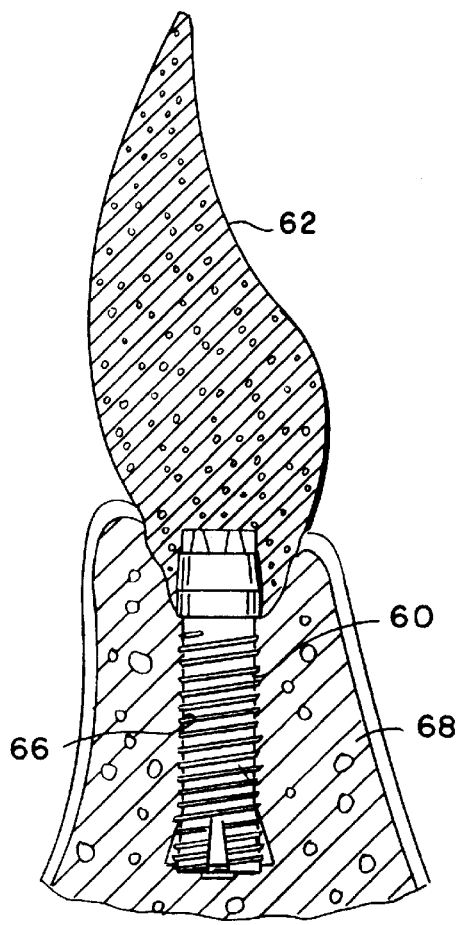
FIG. 1 is a partially fragmented sectional view illustrating a dental implant embedded within a jawbone, the implant including an abutment to which a porcelain crown is attached.

As shown in the drawings for purposes of illustration, the present invention is concerned with a novel implant assembly 60, and a process for preparing a prosthetic device 62 which, ultimately, is fixed to the implant assembly 60. The invention is described below in connection with a dental implant assembly 60 and a related process for preparing a tooth prosthesis 62. It is will be understood, however, that the present invention may be applied to various types of implantable prosthetic devices, and is not limited to dental implants.

Figure 2:
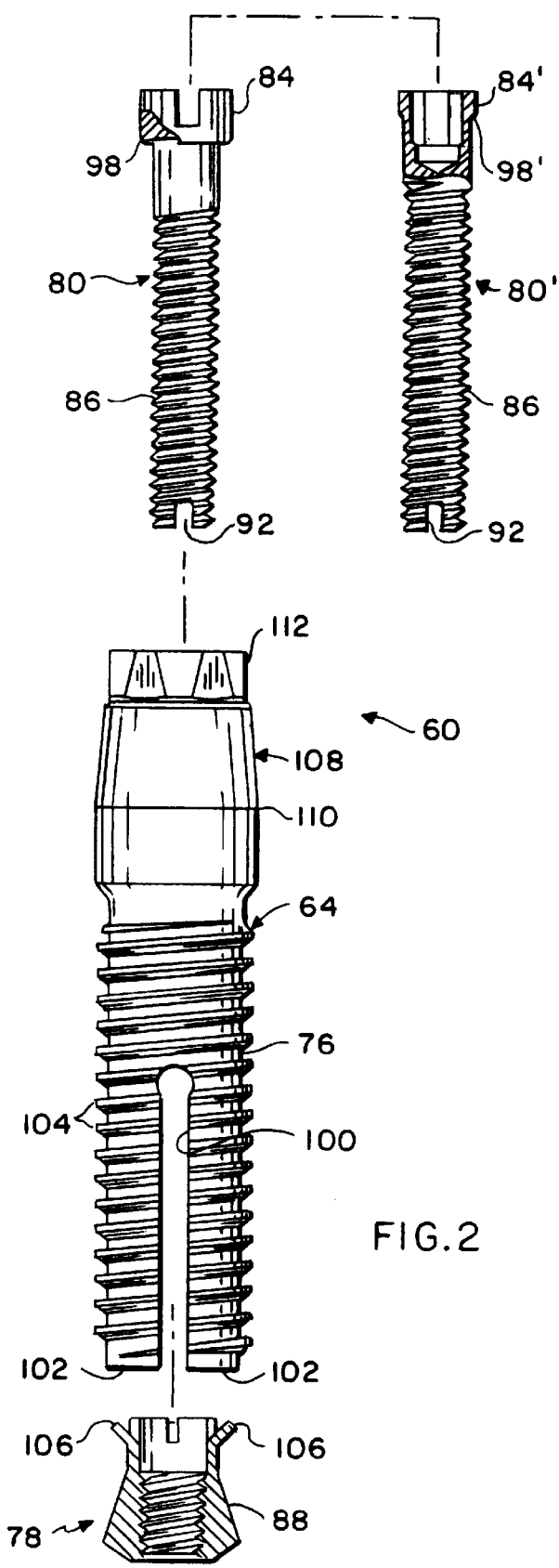
FIG. 2 is an exploded elevational and partially sectional view of the implant assembly of FIG. 1.
Figure 3:
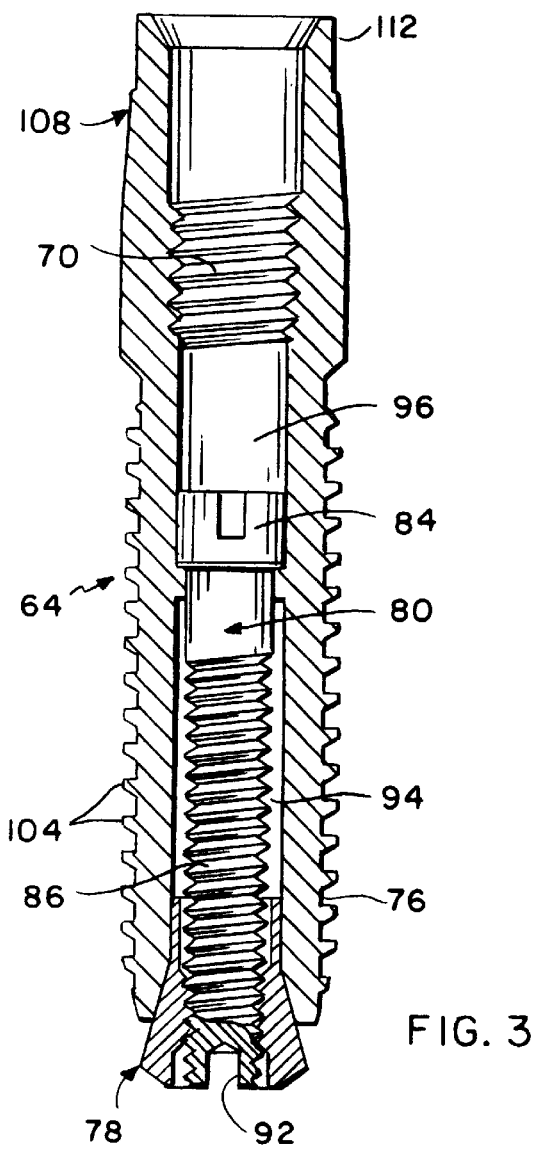
FIG. 3 is an elevational section of the components illustrated in FIG. 2.
Figure 4:
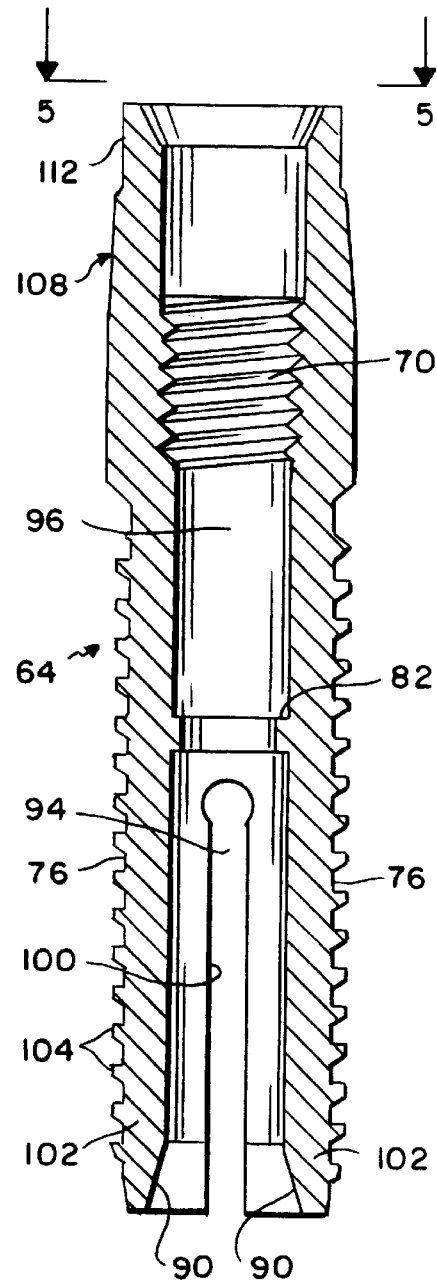
FIG. 4 is an elevational sectional view of the elongated hollow body portion of the implant assembly illustrated in FIGS. 2 and 3.
Figure 5:
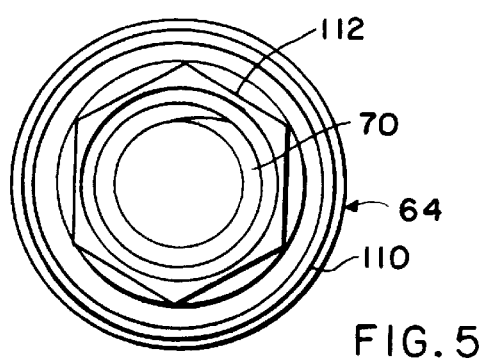
FIG. 5 is a top plan view of the elongated hollow body portion taken generally along the line 5—5 of FIG. 4.

With reference to FIGS. 1–5, the implant assembly 60 comprises an elongated hollow (tubular) body 64 which is receivable within a bore 66 provided in the jawbone 68 of the patient. The tubular body 64 is provided with internal threads 70 which are adapted to threadably receive a threaded shank portion 72 of an abutment post 74, more fully described below in connection with FIGS. 44–51. The tubular body 64 includes a skirt portion 76 radially movable from a first retracted position (shown in FIGS. 2–4) to a second expanded position (shown in FIG. 1). To move the skirt portion 76 into the second expanded position, there is provided expander means shown in the drawings as comprising an expansion nut 78 and a draw screw 80. As shown in FIGS. 3 and 4, the tubular body 64 includes an internal shoulder 82 on which a head 84 of the draw screw 80 rests. A threaded shank portion 86 of the draw screw 80 extends below the shoulder 82 generally to a lower end of the tubular body 64 whereat the expansion nut 78 is threaded onto the threaded shank 86. The expansion nut 78 includes a frustoconically-shaped skirt-engaging side wall 88 which is adapted to engage inwardly sloping or inclined side walls 90 provided on the skirt portion 76 of the tubular body 64.

Referring to FIGS. 2 and 3, the end of the threaded shank 86 includes a slot 92 that permits the end of the draw screw 80 to be enlarged after the expansion nut 78 is threaded thereon. This prevents the expansion nut 78 from being inadvertently disassociated from the draw screw 80 within the bore 66.

FIG. 2 further illustrates two alternative draw screws 80 and 80'. The head 84 of the draw screw 80 is slotted, whereas the head 84' is internally hexed to receive an alien wrench or the like. Importantly, the draw screws 80 and 80' are each configured to sealingly engage the internal shoulder 82 of the elongated hollow body 64 to isolate a first hollow body chamber 94 (defined as the area within the tubular body 64 beneath the shoulder 82 into which the threaded shank 86 extends), from a second hollow body chamber 96 (defined as the interior of the elongated hollow body 64 above the internal shoulder 82). In this regard, the slotted head 84 of the draw screw 80 has a tapered (non-ninety degree) shoulder 98 which, when it engages the internal shoulder 82 as the expansion nut 78 is drawn upwardly into the skirt portion 76, causes a cold weld between the facing portions of the head 84 and the shoulder 82. The head 84' of the draw screw 80' includes a shoulder 98' comprising a 7° Morris taper that likewise seals the first hollow body chamber 94 from the second hollow body chamber 96.

As best shown in FIGS. 2–4, the skirt portion 76 of the tubular body 64 is provided with four circumferentially spaced elongated slits 100 which define four separately-movable bone anchor segments 102 each having bone penetrating means provided in the form of a series of longitudinally spaced, blade-like bone penetrating protuberances 104. As the expansion nut 78 is drawn into the tubular body 64, the bone anchor segments 102 will be expanded outwardly so that penetrating protuberances 104 slice into the bone in a manner to securely lock the tubular body 64 within the bore 66. As the expansion nut 78 is being drawn into the tubular body 64, tabs 106 which extend outwardly from an upper portion of the expansion nut 78 travel upwardly through the elongated slits 100 to prevent rotation of the expansion nut 78 relative to the tubular body 64.

Figure 18:
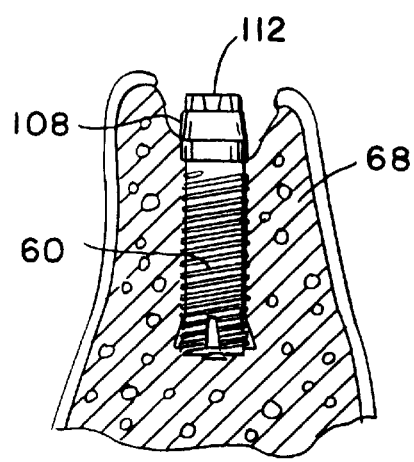

When the implant assembly 60 is properly positioned within the jawbone 68 of the patient as illustrated in FIG. 18, an upper portion of the tubular body 64 comprising an abutment 108 extends upwardly from the jawbone. The abutment 108 includes a cylindrical ring 110 having a diameter generally slightly larger than the diameter of the bore 66, and an uppermost, exteriorly hexagonal collar portion 112.

Prior to placing the implant assembly 60 within the jawbone 68 of a patient, the jawbone is first drilled to provide a bore 66 of a selected diameter, preferably slightly less than the diameter of the cylindrical ring 110. The implant assembly 60 is prepared by simply placing the draw screw 80 within the tubular body 64 so that the head 84 of the draw screw 80 rests against the internal shoulder 82. The expansion nut 78 is threaded onto the bottom end of the threaded shank 86 just enough to ensure that the tabs 106 of the expansion nut 78 will be properly aligned with the elongated slits 100. This assembly of the tubular body 64, the draw screw 80 and the expansion nut 78 is then placed within the bore 66. A screwdriver or alien wrench (depending on the configuration of the head 84 or 84') may be inserted through the upper end of the tubular body 64 to turn the draw screw 80 for the purpose of drawing the expansion nut 78 upwardly into the tubular body 64. If necessary, a wrench may be utilized to engage the upper hex 112 to prevent rotation of the tubular body 64. The tabs 106 ensure that the expansion nut 78 does not rotate relative to the tubular body 64. As the expansion nut 78 is drawn into the tubular body 64, the bone anchor segments 102 expand outwardly so that the penetrating protuberances 104 slice into the bone in a manner to securely lock the tubular body 64 within the bore 66.

Preferably the exterior surfaces of the abutment 108 are plated with titanium nitride to give the abutment 108 a gold color. This is desirable primarily for aesthetic reasons. In some cases, depending on the nature of the patient's gums, a silver abutment would be visible. The gold color of the abutment plated with titanium nitride minimizes shine-through by providing the abutment a more natural color.

FIGS. 6–8 illustrate a waxing sleeve 114. The function of the waxing sleeve will be fully described below in connection with the process steps illustrated in FIGS. 28–31. The waxing sleeve 114 is preferably manufactured of a clear plastic material that may be burned-off with a wax-up of a dental crown or other prosthetic device 62 to be manufactured utilizing standard casting procedures. The waxing sleeve 114 is generally cylindrical having an open upper end 116 and an open lower end 118. A plurality of circumferential rings 120 are provided to facilitate handling of the waxing sleeve 114. An inner hexed surface 122 is provided within an internal cavity 124, and is configured to mate with a like-shaped upper collar 126 of an implant analog 128 (shown in FIGS. 15–17). The upper collar 126 of the implant analog 128 corresponds in shape to the upper hex collar 112 of the abutment 108. Adjacent the inner hexed surface 122, the internal cavity 124 includes an inner shoulder 130 which is configured to engage an upper end of the upper collar 126 of the implant analog 128.

FIGS. 9–11 illustrate a treatment crown sleeve 132. The treatment crown sleeve 132 is typically manufactured of the same hardened metals comprising the tubular body 64, and comprises a generally tubular main body 134. A plurality of circumferentially extending rings 136 are provided to facilitate handling of the treatment crown sleeve 132, and further to facilitate bonding of composite materials thereto. Use of the treatment crown sleeve 132 will be further described below in connection with the process steps illustrated in FIGS. 22 and 23.

The inner configuration of the treatment crown sleeve 132 is identical to the inner configuration of the lower portion of the waxing sleeve 114. In this regard, the treatment crown sleeve 132 includes an inner hexed surface 138 having a configuration designed to mate precisely with the outer hexed surface 112 of the abutment 108. Further, an inner shoulder 140 is provided adjacent to the inner hexed surface 138 to provide an inner seating surface for the treatment crown sleeve 132 on an upper surface of the abutment 108. Like the abutment 108, the treatment crown sleeve 132 is preferably plated with a titanium nitride material to give it a gold color for the same reasons discussed above.

Figure 13:
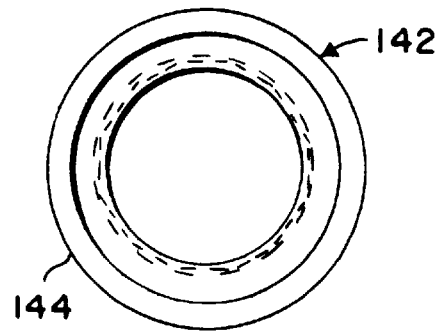
FIG. 13 is a top plan view of the transfer sleeve taken generally along the line 13—13 of FIG. 12.
Figure 12:
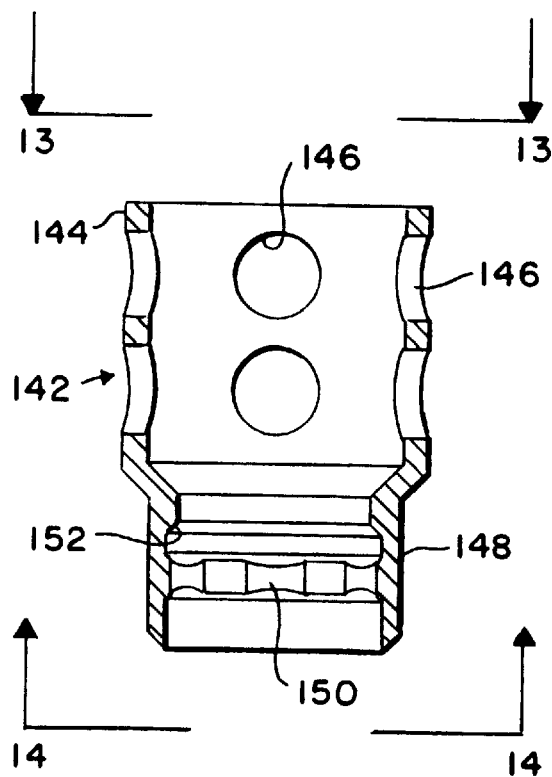
FIG. 12 is an elevational sectional view of a transfer sleeve, the use of which is more fully described in connection with the discussion of FIGS. 19–21 and 24–26.
Figure 14:
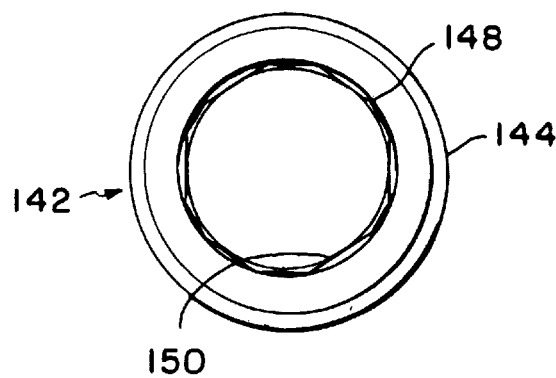
FIG. 14 is a bottom plan view of the transfer sleeve taken generally taken along the line 14—14 of FIG. 12.

FIGS. 12–14 illustrate a transfer sleeve 142. The function of the transfer sleeve will be described fully below in connection with process steps illustrated in FIGS. 19–21 and 24–26. The transfer sleeve 142 includes a generally cylindrical upper portion 144 having a plurality of apertures 146 therethrough, and a reduced diameter lower portion 148 (relative to the upper portion 144) which is, essentially, a shortened version of the treatment crown sleeve 132. The lower portion 148 includes an inner hexed surface 150 for matingly engaging the upper collar 112 of the abutment 108. Further, an inner shoulder 152 is provided to rest directly upon an upper end of the upper hex collar 112.

It should be understood that the inner configuration of the inner hexed surfaces and inner shoulders of the waxing sleeve 114, the treatment crown sleeve 132, and the transfer sleeve 142 are identical. It is intended that each of these components fit in precisely the same way upon the identical upper hex collars 112 and 126 of the abutment 108 and the implant analog 128.

Figure 17:
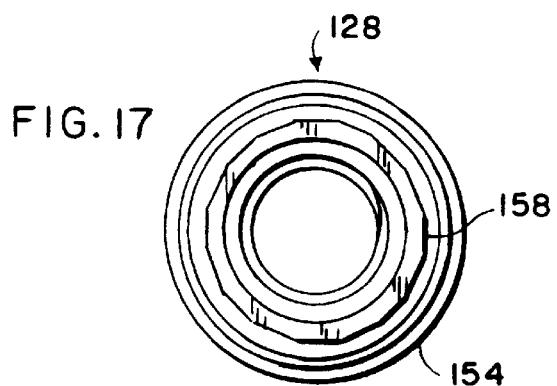
FIG. 17 is a top plan view of the implant analog taken generally along the line 17—17 of FIG. 15.
Figure 15:
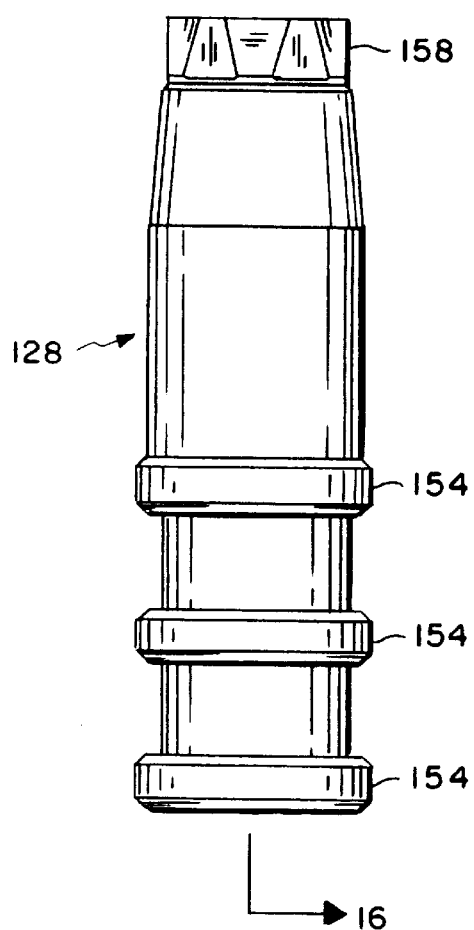
FIG. 15 is an elevational view of an implant analog whose use is discussed in connection with the description of FIGS. 24–31.
Figure 16:
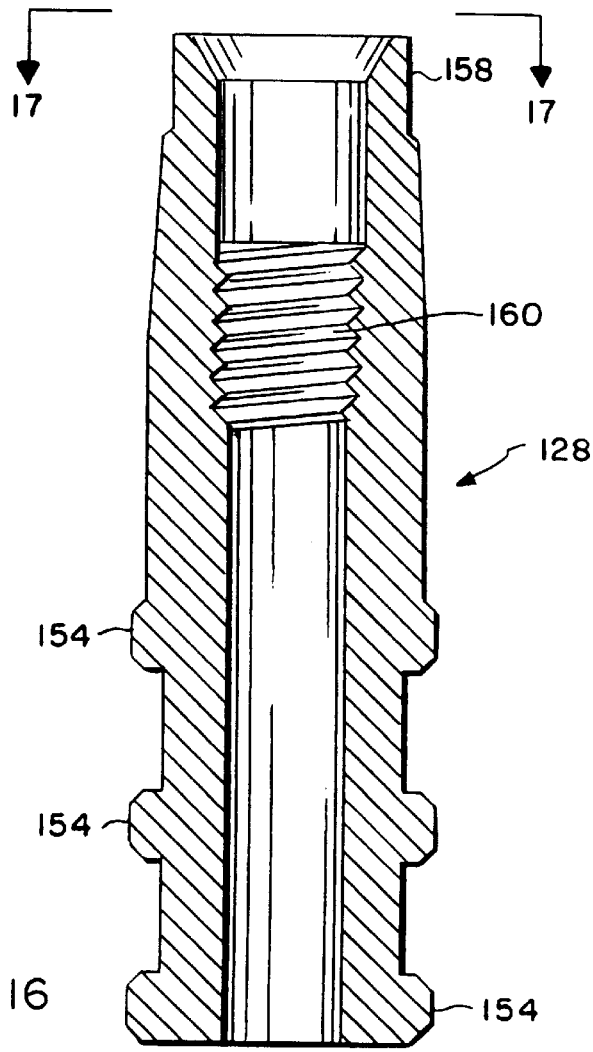
FIG. 16 is an enlarged sectional view taken generally along the line 16—16 of FIG. 15.

FIGS. 15–17 illustrate the implant analog 128. The function of the implant analog 128 will be described below in connection with the process steps illustrated in FIGS. 24–31. The implant analog 128 comprises a generally tubular body which has three circumferentially extending rings 154. The lower portion of the implant analog 128 is configured simply for ease in handling and for securement within a stone mold 156 (see FIG. 27). The upper portion 158 of the implant analog 128 duplicates the exterior configuration of the abutment 108. Further, the implant analog 128 includes a longitudinally extending central cavity that defines internal threads 160 that correspond in placement to the internal threads 70 in the tubular body 64.

Figure 19:
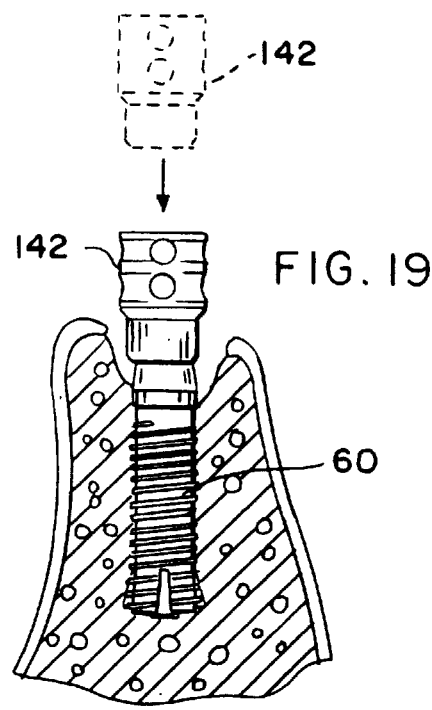

Turning to FIGS. 18–32, the process for preparing a prosthesis in accordance with the present invention will now be described, with particular reference to a tooth prosthesis. First, the implant assembly 60 is positioned within the bore 66 in the jawbone 68 as described above and illustrated in FIG. 18. Next, as shown in FIG. 19, the transfer sleeve 142 is placed over the abutment 108 so that the inner shoulder 152 rests upon the upper edge of the abutment 108 and so that the inner hexed surface 150 engages the hexed outer surface 112.

Figure 20:
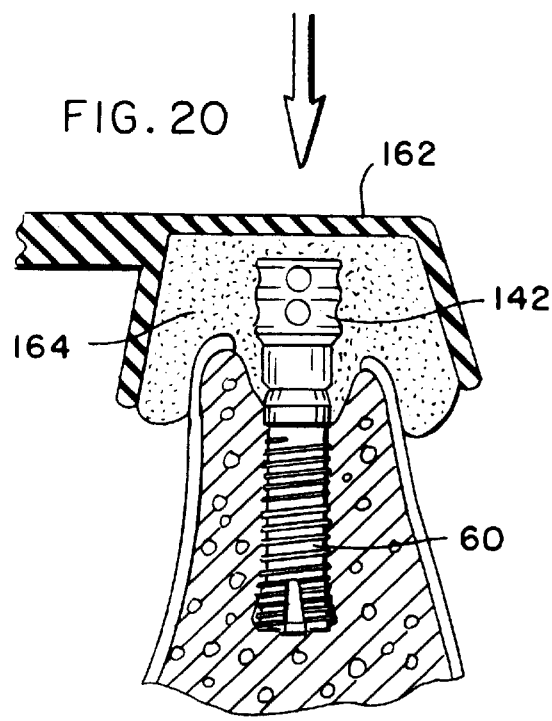
Figure 21:
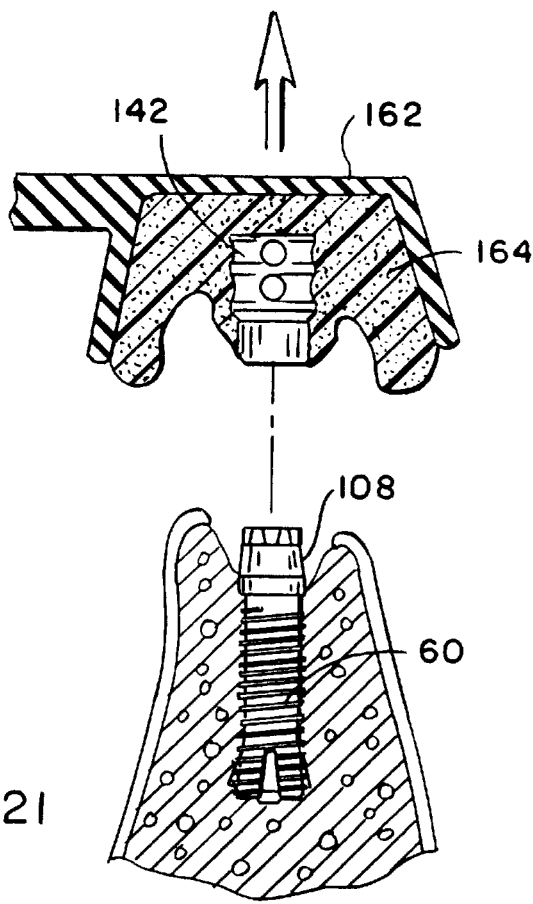

As illustrated in FIGS. 20 and 21, a suitable holder 162 is filled with impression material 164, and an impression is taken of the mouth. As the impression material 164 is removed from the mouth, the transfer sleeve 142 is also removed from the abutment 108.

With reference to FIGS. 22 and 23, immediate provisionalization can be accomplished following implant assembly 60 placement when the supporting bone is of good quality (type I, II and frequently III) and the aesthetic and/or psychological needs of the patient dictate. In this regard, a custom acrylic resin crown or fixed prosthesis can be made beforehand from waxed-corrected casts of the patient's dentition. For single units, a hollowed-out, properly selected acrylic resin denture tooth 166 may be used as an alternative. The treatment crown sleeve 132 is utilized in connection with this immediate provisionalization. The denture tooth 166 is filled with a composite material, and the treatment crown sleeve 132 is placed over the abutment 108 so that the inner hexed surface 138 fully engages the upper hex collar 112 of the abutment 108. A cold cure acrylic resin 168 is placed within the denture tooth 166 (provisional restoration). When the acrylic resin 168 begins to set, the provisional 166 is placed over the abutment 108 and the treatment crown sleeve 132, making certain to align the provisional 166 with the adjacent teeth. After the acrylic resin 168 has set, the provisional denture tooth 170 is removed from the mouth. The provisional tooth 170 now incorporates the treatment crown sleeve 132. The treatment crown sleeve 132 provides internal titanium strength, better frictional retention and a precision fit margin for the provisional tooth 170. The provisional tooth 170 may then be contoured, polished and adjusted as necessary to establish a natural anatomic profile. The provisional tooth 170 may then be reattached over the abutment 108 until a permanent crown is prepared as discussed below.

Figure 26:
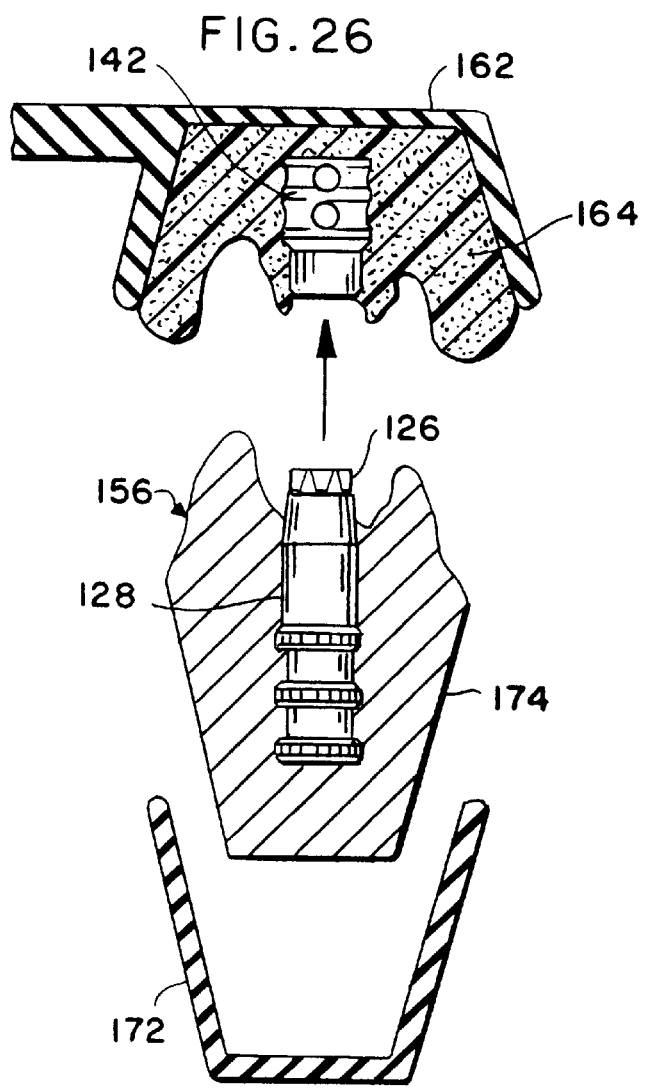
Figure 28:
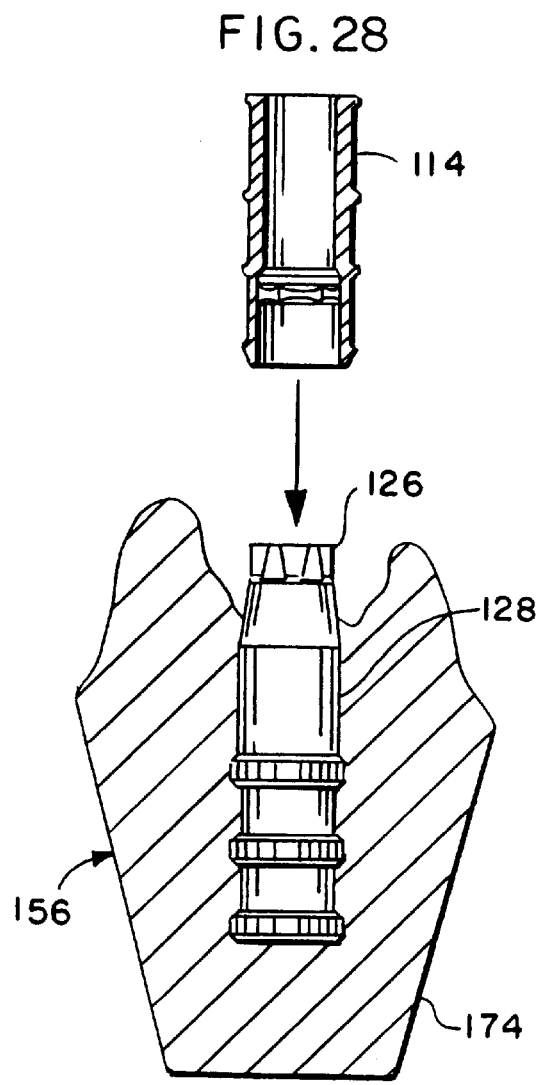
Figure 27:
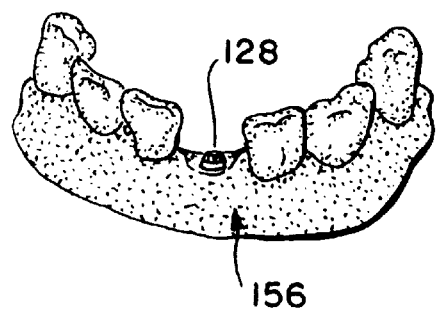
Figure 29:
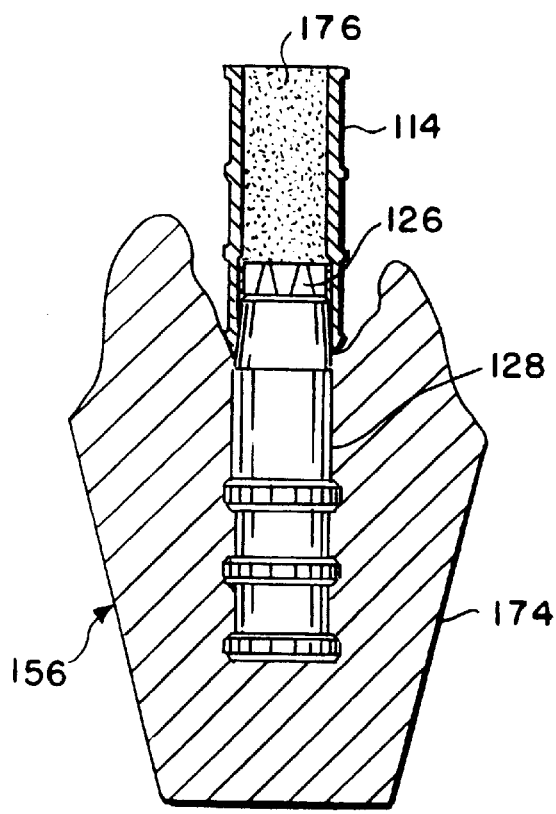

Referring now to FIGS. 24–27, the implant analog 128 is placed into the transfer sleeve 142 (FIG. 24). A cast 172 is utilized and stone 174 is poured within the cast over the exposed portion of the implant analog 128 (FIG. 25). Once the stone 174 has set-up, the holder 162 and impression material 164 containing the transfer sleeve 142 are removed from the implant analog 128, and the cast 172 is removed from the stone 174 (FIG. 26). The result is a stone mold 156 which is an exact model of the mouth (FIG. 27).

Figure 30:
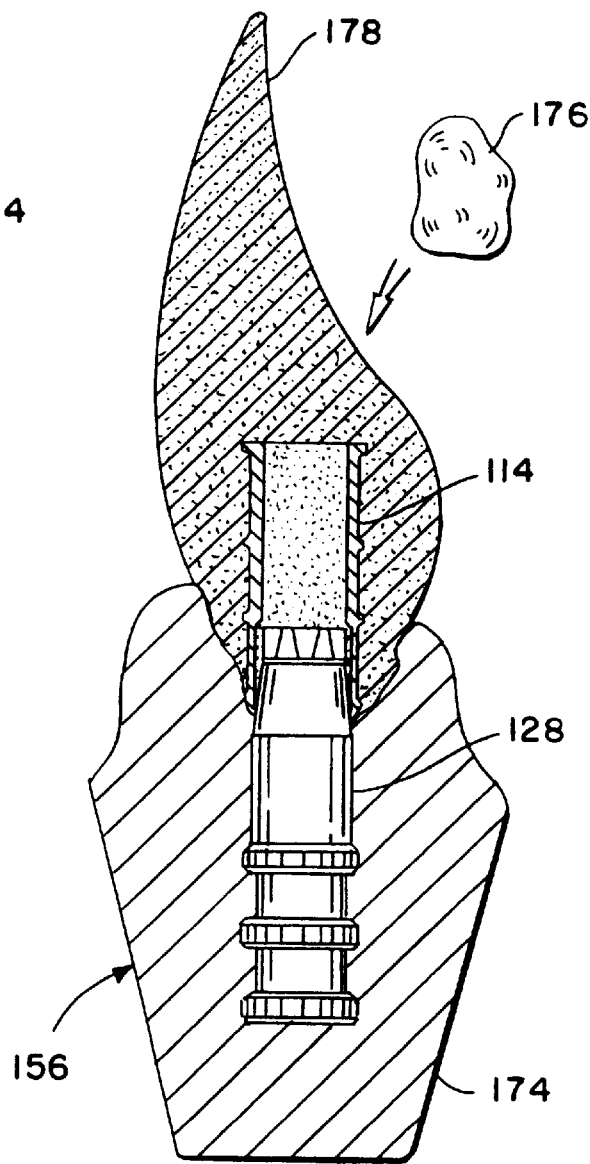

Next, the waxing sleeve 114 is placed over the implant analog 128 (FIG. 28) so that the inner hexed surface 122 fully engages the upper collar 126 of the implant analog 128. The waxing sleeve 114 is then filled with wax 176 (FIG. 29), and then a wax-up 178 in the shape of a tooth is formed in the standard fashion (FIG. 30). The wax-up 178, including the waxing sleeve 114 is then removed from the implant analog 128 (FIG. 31) and placed in investment stone for purposes of forming a crown in a manner well known to those of ordinary skill in the art. During the manufacture of a crown 180 corresponding in shape to the wax-up 178, the wax 176 and the waxing sleeve 114 are burned off. The resulting crown 180 has an internal cavity 182 exactly configured to match the exposed portion of the abutment 108. Finally, an adhesive 184 is placed within the internal cavity 182, and the crown 180 is secured to the abutment 108 (FIG. 32). The resulting structure is illustrated in FIG. 1.

Figure 33:
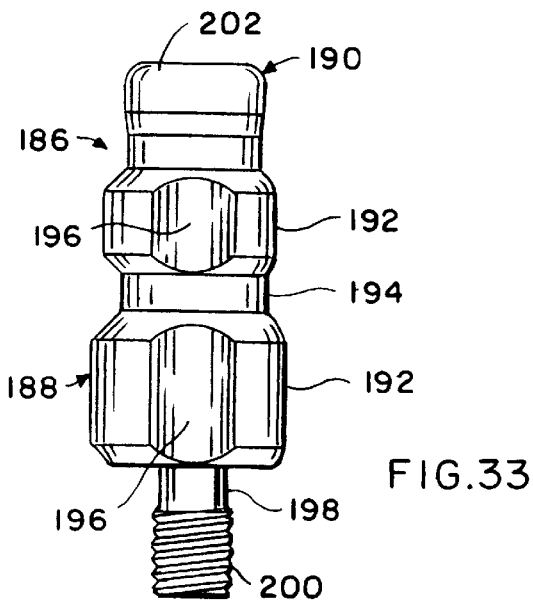
Figure 38:
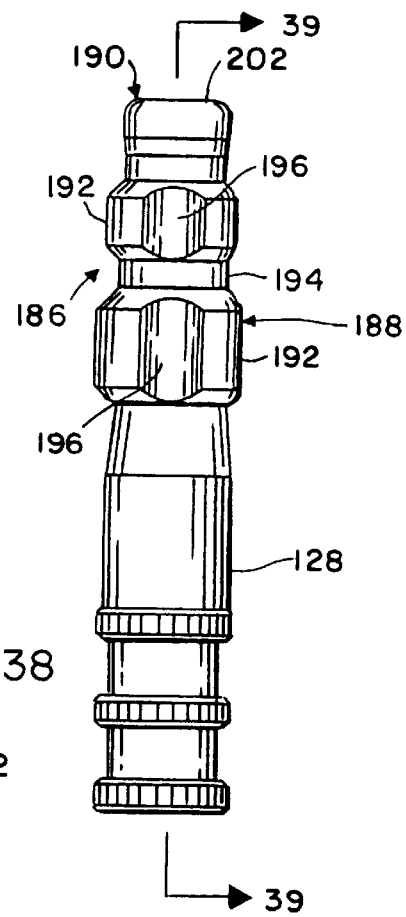
Figure 39:
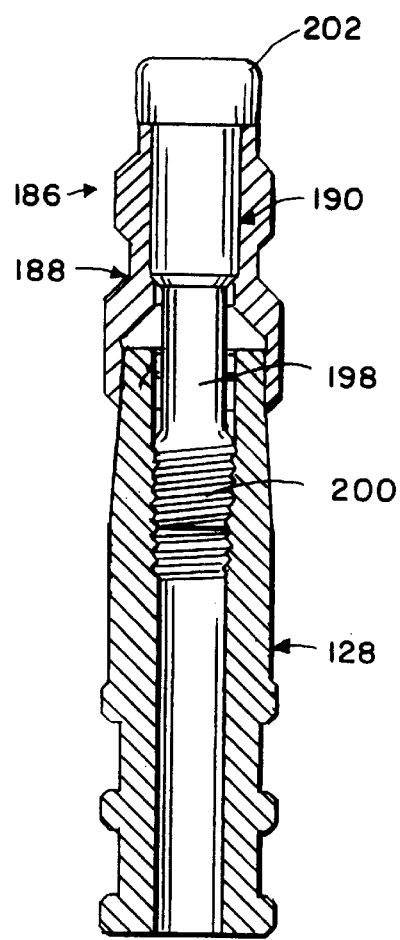

FIGS. 33, 38 and 39 illustrate an impression post assembly 186 that is utilized in connection with an alternative process for preparing a prosthesis in accordance with the present invention. The impression post assembly 186 comprises, in its simplest form, two primary components, namely, a generally tubular skirt 188 and a retention screw or post 190. The skirt 188 exteriorly forms a pair of rings 192 separated by a channel 194. The rings are provided detents 196 to facilitate handling of the skirt 188 and the forming of an impression thereover, as will be described below. Interiorly, the skirt 188 forms a recess for receiving a shank portion 198 of the retention post 190. The lower end 200 of the shank portion 198 is threaded for reception by the internal threads 160 of the implant analog 128 (FIG. 39), or the internal threads 70 of the elongated hollow body 64. The upper end of the retention post 190 includes a head 202 whose diameter generally matches the diameter of the upper end of the skirt 188. The lower end of the skirt 188 is interiorly configured to match the upper hexed collar 112 of the abutment 108 and the upper collar 126 of the implant analog 128. Thus, when the impression post assembly 186 is properly positioned over either the abutment 108 or the implant analog 128, the lower portion of the skirt 188 overlies the upper collars 112 or 126.

Figure 34:
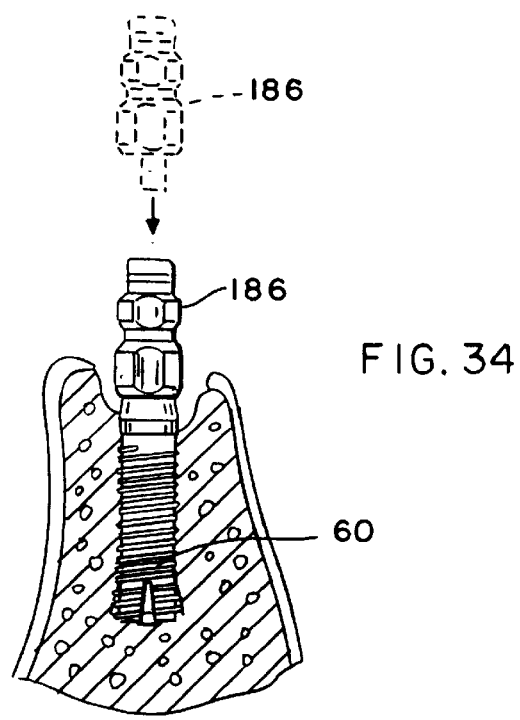

Turning now to FIGS. 34–43, the alternative process for preparing a prosthesis in accordance with the present invention will be described, again with particular reference to a tooth prosthesis. As was the case with the process described above, the first step is to position the implant assembly 60 within the bore 66 in the jaw bone 68. Next, as shown in FIG. 34, the impression post assembly 186 is placed over the abutment 108 so that the upper hexed collar 112 of the abutment 108 is received within the skirt 188 and such that the lower threaded end 200 of the retention post 190 is secured within the internal threads 70 of the elongated hollow body 64.

Figure 35:
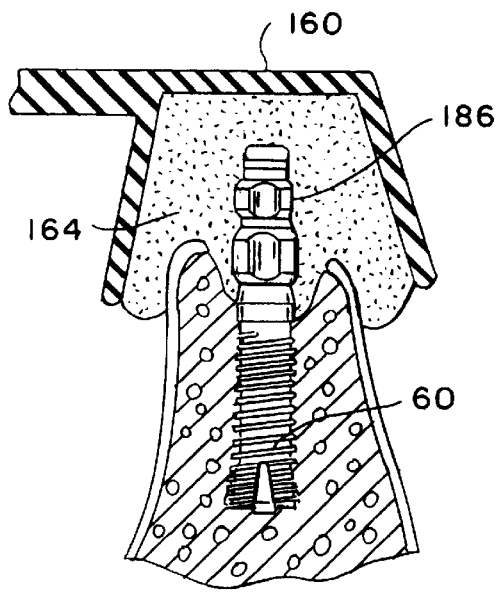
Figure 36:
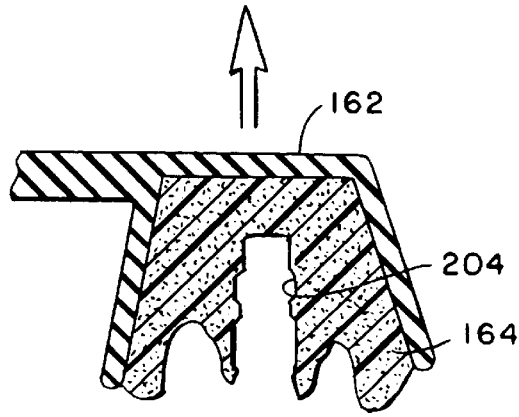
Figure 37:
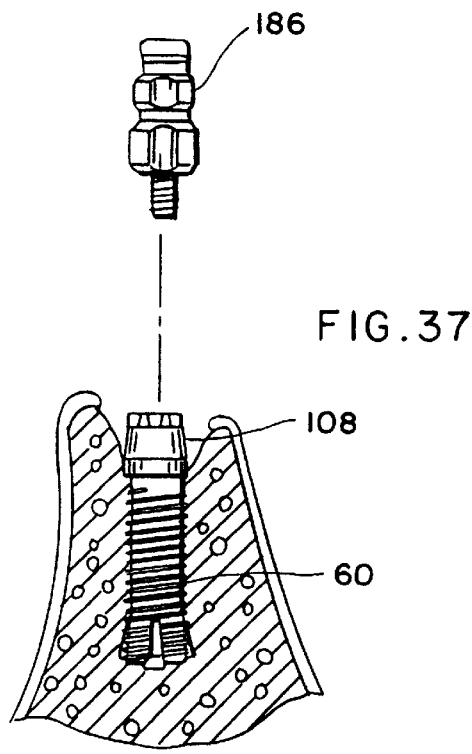

As illustrated in FIGS. 35 and 36, a suitable holder 162 is filled with impression material 164, and an impression is taken of the mouth. As the impression material 164 is removed from the mouth, the impression post assembly 186, unlike the transfer sleeve 142, remains affixed to the abutment 108. As illustrated in FIGS. 37–39, the impression post assembly 186 is then removed from the abutment 108 and secured in a like manner to the implant analog 128.

At this point, immediate provisionalization can be accomplished following implant assembly 60 placement when the supporting bone is of good quality (type I, II and frequently III) and the aesthetic and/or psychological needs of the patient dictate. The steps discussed above with reference to FIGS. 22 and 23 would be followed in this regard.

Referring now to FIGS. 40–43, the implant analog 128 having the attached impression post assembly 126 is placed into the impression 204 of the impression post assembly 186 in the impression material 164 (FIG. 40). A cast 172 is utilized and stone 174 is poured within the cast over the exposed portion of the implant analog 128 (FIG. 41). Once the stone 174 has set -up, the holder 162 and impression material 164 are removed from the implant analog 128 and the attached impression post assembly 186, and the cast 172 is removed from the stone 174 (FIG. 42). The result is a stone mold 156 which, when the impression post assembly 186 is removed from the implant analog 128 (FIG. 43) is an exact model of the mouth.

To complete the process, the same steps as discussed above in connection with FIGS. 28–32 are followed. Namely, the waxing sleeve 114 is placed over the implant analog 128 (FIG. 28) so that the inner hexed surface 122 fully engages the upper collar 126 of the implant analog 128. The waxing sleeve 114 is then filled with wax 176 (FIG. 29), and then a wax-up 178 in the shape of a tooth is formed in the standard fashion (FIG. 30). The wax-up 178, including the waxing sleeve 114 is then removed from the implant analog 128 (FIG. 31) and placed in investment stone for purposes of forming a crown in a manner well known to those of ordinary skill in the art. During the manufacture of a crown 180 corresponding in shape to the wax-up 178, the wax 176 and the waxing sleeve 114 are burned off. The resulting crown 180 has an internal cavity 182 exactly configured to match the exposed portion of the abutment 108. Finally, an adhesive 184 is placed within the internal cavity 182, and the crown 180 is secured to the abutment 108 (FIG. 32). The resulting structure is illustrated in FIG. 1.

A common feature in both of the above-described processes embodying aspects of the present invention is the use of a transfer component utilized in the taking of the impression 204 and in the creation of the stone mold 156. In the first process described above, the transfer component comprises the transfer sleeve 142. In the second process described above, the transfer component comprises the impression post assembly 186. It will be understood by those of skill in the art, however, that other types of transfer components may be utilized which are not necessarily identical to the two transfer components specifically illustrated and described herein.

As illustrated in FIGS. 44–51 abutment posts 74–74" may be advantageously utilized particularly in connection with the process for preparing a tooth prosthesis illustrated in FIGS. 18–32. The abutment posts 74–74" are utilized in much the same manner as a similar component as used and described in U.S. Pat. No. 5,681,167, the contents of which are incorporated herein.

Figures 44, 45:
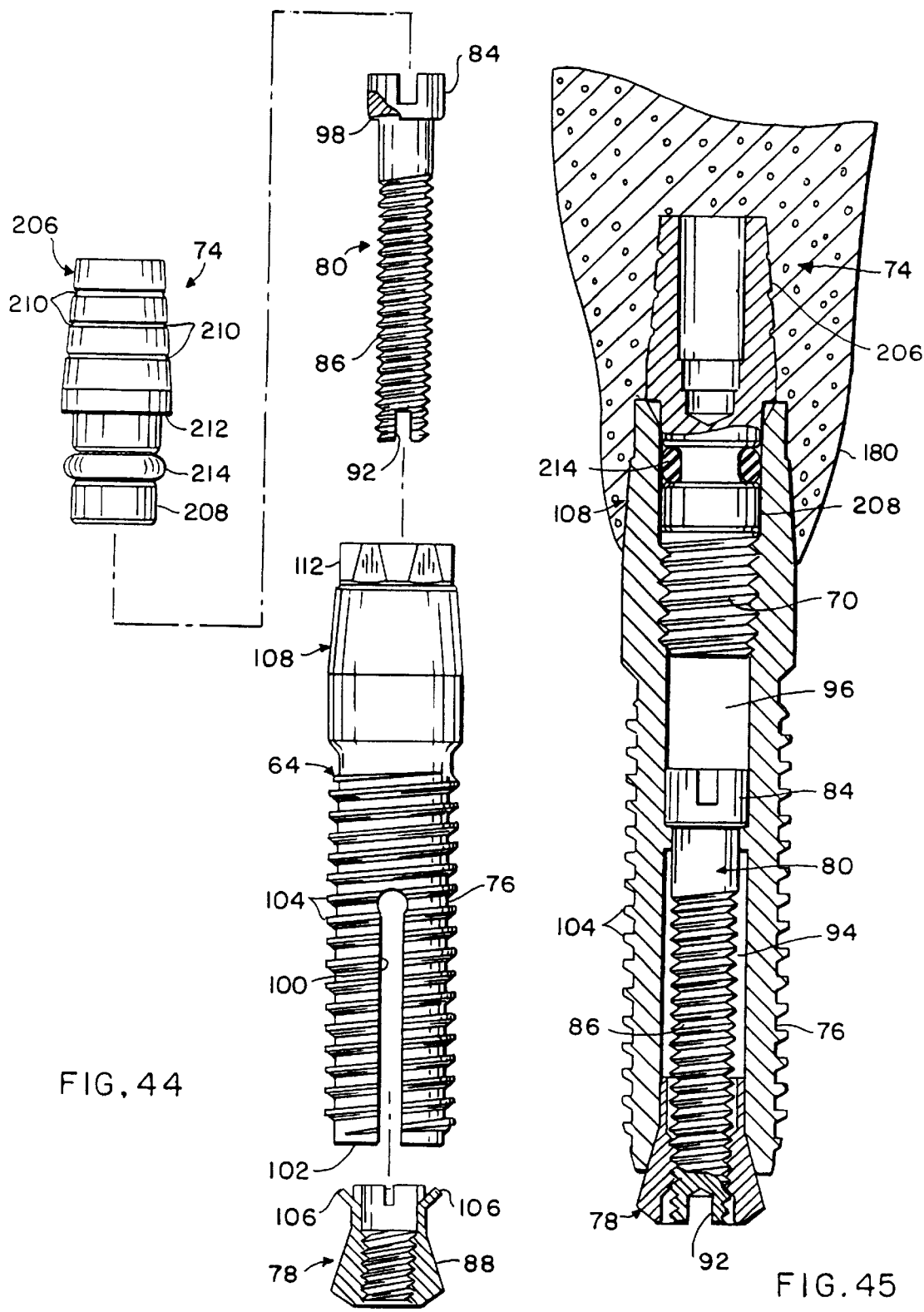
FIG. 44 is an exploded elevational and partially sectional view of an implant assembly similar to that illustrated in FIG. 2, illustrating the addition of an abutment post that may be press-fit into the elongated hollow body.
FIG. 45 is an elevational section of the components illustrated in FIG. 44, illustrating attachment of the abutment post to the elongated hollow body and securement of a prosthetic component to the abutment and the abutment post.
Figure 46:
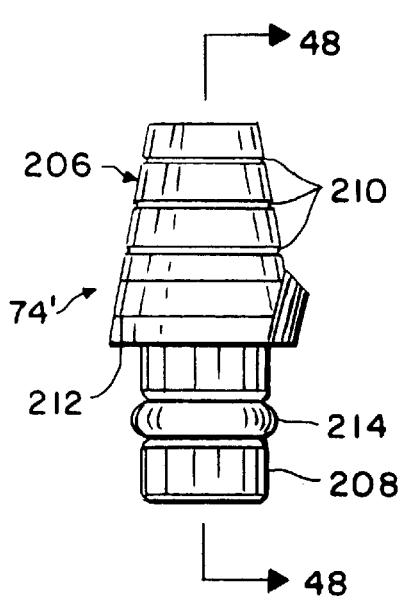
FIG. 46 is an elevational view of an alternative form of the abutment post illustrated in FIGS. 44 and 45.
Figure 48:
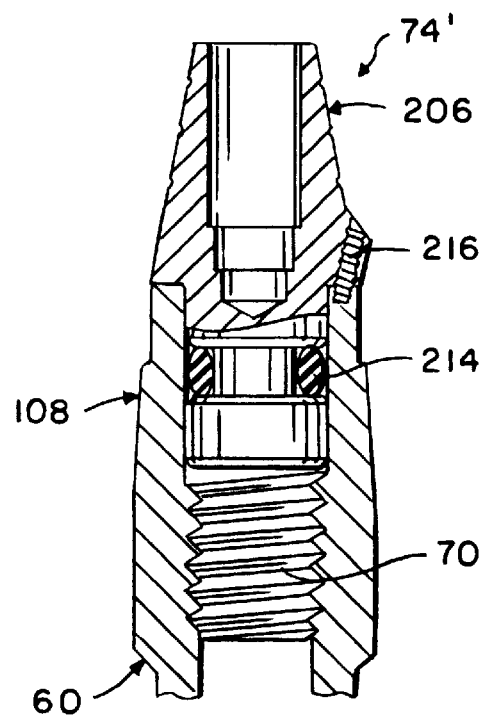
FIG. 48 is a partially fragmented sectional view taken generally along the line 48—48 of FIG. 46, illustrating the abutment post seated over the abutment portion of the elongated hollow body of FIGS. 44 and 45.
Figure 47:
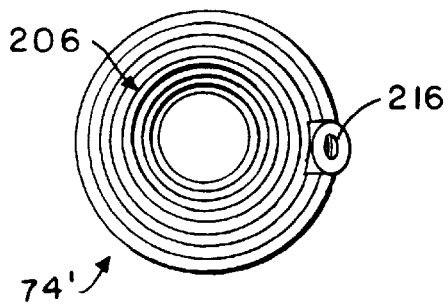
FIG. 47 is a top plan view taken generally along the line 47—47 of FIG. 46.
Figure 49:
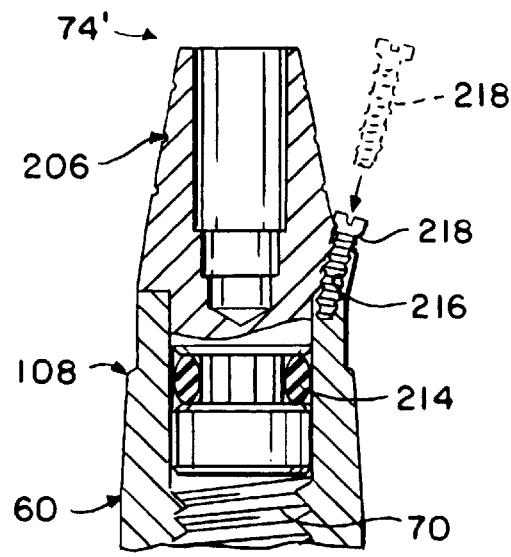
FIG. 49 is a view similar to that shown in FIG. 48, illustrating the manner in which a screw may be threaded into an inclined threaded passageway to assist in removal of the abutment post from the abutment.

With reference to FIGS. 44 and 45, the modified implant assembly 60 comprises an elongated hollow (tubular) body 64 which is receivable within a bore 66 provided in the jaw bone 68 of the patient, an expansion nut 78 and a draw screw 80, all of which are identical to those components described in connection with FIGS. 1–5 above. The abutment post 74 includes a head 206 and a shaft 208 that extends downwardly from the head 206. The head 206 has a frusto-conical outer surface with a plurality of circumferentially grooves 210 which assist in chair-side modification of the shape of the abutment post. The head 206 further includes a shoulder 212 which defines a transition area between the outer frusto-conical surface of the head and a generally cylindrical outer surface thereof which is positioned within the abutment 108. An O-ring 214 is positioned within a circumferential groove in the shaft 208 to facilitate press-fit reception of the shaft 208 within the abutment 108 (FIG. 45). Use of the abutment post 74 illustrated in FIGS. 44 and 45 facilitates press-fit connection of the crown 180 over the abutment 108 and subsequent attachment thereto by means of cement or another adhesive.

FIGS. 46–49 illustrate another type of abutment post 74' that is similar to the abutment post 74 illustrated in FIGS. 44 and 45. As such, like elements will retain the same numerical designation. More particularly, the abutment post 74' includes a head 206 and a shaft 208 that extends from the head 206 downwardly. The head 206 has a frusto-conical outer surface with a plurality of circumferentially extending grooves 210 which assist in chair-side modification of the shape of the abutment assembly. The head 206 further includes a shoulder 212 which defines a transition area between the outer frusto-conical surface of the head and a generally cylindrical outer surface thereof which is positioned within the abutment 108. An O-ring 214 is positioned within a circumferentially extending groove about the shaft 208 to facilitate press-fit reception within the abutment 108, as shown.

The primary modification is the inclusion of an internally threaded, externally accessible cavity 216 through the head 206, whose longitudinal axis is inclined from the longitudinal axis of the abutment post 74'. The lower end of the cavity 216 is positioned adjacent to the upper end of the upper collar 112 of the abutment 108 to facilitate removal of the abutment post 74' from the abutment 108 if needed.

More particularly, it may be the case where the dentist adheres the abutment post 74' in place to the abutment 108, and later desires to remove the abutment post 74'. Such removal may be facilitated by threading a screw 218 into the threaded cavity 216 until a lower end thereof contacts the upper edge of the upper collar 112 of the abutment 108. By further turning the screw 218 into the cavity 216, the lower edge of the shoulder 212 will be pulled away from the upper edge of the upper collar 112 of the abutment 108, thereby effecting the desired separation.

FIGS. 50 and 51 are similar to FIGS. 44 and 45, and illustrate yet another type of abutment post 74" utilized in connection with the implant assembly 60. Again, the elongated hollow (tubular) body 64, the expansion nut 78 and the draw screw 80 are identical to those described above. Here, the difference lies in the provision of a threaded, plug-type abutment post 74" that is configured to be received entirely within the abutment 108. The plug-type abutment post 74" includes an upper body portion 220 whose external configuration matches the internal configuration of the upper portion of the abutment 108, and a lower threaded portion 222 that may be received within the internal threads 70 of the tubular body 64. The upper body portion 220 further includes an internally threaded recess 224 that is configured to receive a screw 226 that may be embedded within the crown 180 during manufacture thereof. This particular arrangement permits the crown 180 to be screw-retained to the abutment 108 by means of threading the screw 226 into the internally threaded recess 224 of the abutment post 74" (FIG. 51).

From the foregoing it is to be appreciated that the present invention provides a novel dental implant assembly useful in a process which permits conditions within the mouth, including the configuration of the dental implant assembly, to be exactly replicated in a stone mold 156. This permits a laboratory technician to accurately manufacture a crown 180 that will properly fit when placed within the patient's mouth. Advantageously, the implant assemblies 60 and the novel processes described above may be utilized in connection with the apparatus and processes described in U.S. Pat. No. 5,681,167 and in connection with prosthetic devices other than dental implants. The prosthetic device 62 may be press-fit, screw retained or cement-retained to the implant assembly 60, thus giving the medical practitioner great flexibility in addressing the needs of the patient.

Although several particular embodiments of the invention have been described in detail for purposes of illustration, various modifications of each may be made without departing from the spirit and scope of the invention. Accordingly, the invention is not to be limited, except as by the appended claims.

I claim:

1. An implant assembly, comprising:
   an elongated hollow body including a skirt receivable within a bore provided in a bone of a patient, an internal shoulder, and an abutment extending from the skirt outwardly from the bore for supporting a prosthetic component, wherein the skirt is radially movable within the bore from a first retracted position to a second expanded position;
   a draw screw having a head captured within the hollow body that engages the internal shoulder to form a seal which isolates a first hollow body chamber on one side of the draw screw head form a second hollow body chamber on an opposite side thereof, and a threaded shank connected to the head and which extends to an end of the skirt; and
   an expansion nut having a skirt-engaging side wall and an inner threaded cavity into which the shank of the draw screw is threaded, whereby rotation of the draw screw through the inner cavity of the expansion nut causes radial movement of the skirt from the first retracted position to the second expanded position.

2. The implant assembly of claim 1, wherein an end of the draw screw threaded shank opposite the draw screw head is enlarged to prevent withdrawal of the threaded shank from the expansion nut.

3. The implant assembly of the claim 1, wherein the skirt includes an inclined internal surface, and wherein the skirt-engaging side wall of the expansion nut has an inclined external surface moveable into engagement with the inclined internal surface of the skirt upon rotation of the draw screw through the inner cavity of the expansion nut.

4. The implant assembly of claim 1, wherein the skirt comprises at least two anchor segments moveable from the first retracted position to the second expanded position.

5. The implant assembly of claim 3, wherein the anchor segments include bone penetrating means for penetrating the bone of the patient upon movement of the segments into the second expanded position.

6. The implant assembly of claim 3, wherein the skirt includes a plurality of circumferentially spaced, longitudinally extending slits which separate the anchor segments.

7. The implant assembly of claim 6, wherein the expansion nut includes a plurality of tabs configured for alignment with the longitudinally extending slits.

8. The implant assembly of claim 1, wherein the draw screw is accessible through the abutment.

9. The implant assembly of claim 1, wherein the abutment includes at least one radially outwardly facing planar surface that may be engaged by the prosthetic component to prevent relative rotation therebetween.

10. The implant assembly of claim 9, wherein the abutment includes a ring having a diameter larger than the bore, wherein the ring provides a shoulder facing the bore, and an upper hexed portion opposite the skirt relative to the ring and presenting a plurality of radially outwardly facing planar surfaces.

11. The implant assembly of claim 1, including an abutment post having a head positioned adjacent to the abutment and a shank received within the hollow body.

12. The implant assembly of claim 11, wherein the abutment post is plated with a gold-colored material.

13. The implant assembly of claim 11, wherein the abutment post includes an O-ring encircling a portion of the abutment post shank, and wherein the abutment post shank is press-fit into the hollow body.

14. The implant assembly of claim 11, wherein the abutment post shank is threadably received within the hollow body.

15. The implant assembly of claim 14, wherein the abutment post head includes an internally threaded, externally accessible cavity capable of threadably receiving a screw therein.

16. The implant assembly of claim 11, wherein the abutment post head has a longitudinal axis and includes a threaded aperture therethrough having an axis inclined from the longitudinal axis of the abutment post head, the threaded aperture has an externally accessible first open end and a second open end positioned adjacent to the abutment.

17. An implant assembly, comprising:

an elongated hollow body including a skirt receivable within a bore provided in a bone of a patient, an internal shoulder, and an abutment extending from the skirt outwardly from the bore for supporting a prosthetic component, wherein the skirt is radially movable within the bore from a first retracted position to a second expanded position;

means for causing radial movement of the skirt from the first retracted position to the second expanded position; and an abutment post having a head positioned adjacent to the abutment and a shank received within the hollow body;

wherein the skirt radial movement means comprises a draw screw having a head captured within the hollow body that engages the internal shoulder to form a seal which isolates a first hollow body chamber on one side of the draw screw head from a second hollow body chamber on an opposite side thereof, and a threaded shank connected to the head which extends to an end of the skirt, and an expansion nut having a skirt-engaging side wall and an inner threaded cavity into which the shank of the draw screw is threaded, whereby rotation of the draw screw through the inner cavity of the expansion nut causes radial movement of the skirt from the first retracted position to the second expanded position.

18. The implant assembly of claim 17, wherein an end of the draw screw threaded shank opposite the draw screw head is enlarged to prevent withdrawal of the threaded shank from the expansion nut.

19. The implant assembly of claim 17, wherein the skirt comprises at least two anchor segments moveable from the first retracted position to the second expanded position, and an inclined internal surface, and wherein the skirt-engaging side wall of the expansion nut has an inclined external surface moveable into engagement with the inclined internal surface of the skirt upon rotation of the draw screw through the inner cavity of the expansion nut.

20. The implant assembly of claim 20, wherein the skirt includes a plurality of circumferentially spaced, longitudinally extending slits which separate the anchor segments, and wherein the expansion nut includes a plurality of tabs configured for alignment with the longitudinally extending slits.

21. An implant assembly, comprising:

an elongated hollow body including a skirt receivable within a bore provided in a bone of a patient, an internal shoulder, and an abutment extending from the skirt outwardly from the bore for supporting a prosthetic component, wherein the skirt is radially movable within the bore from a first retracted position to a second expanded position, the abutment includes a ring having a diameter larger than the bore, and wherein the ring provides a shoulder facing the bore, and an upper hexed portion opposite the skirt relative to the ring and presenting a plurality of radially outwardly facing planar surfaces;

means for causing radial movement of the skirt from the first retracted position to the second expanded position; and an abutment post having a head positioned adjacent to the abutment and a shank received within the hollow body.

22. An implant assembly, comprising:

an elongated hollow body including a skirt receivable within a bore provided in a bone of a patient, an internal shoulder, and an abutment extending from the skirt outwardly from the bore for supporting a prosthetic component, wherein the skirt is radially movable within the bore from a first retracted position to a second expanded position;

means for causing radial movement of the skirt from the first retracted position to the second expanded position; and an abutment post having a head positioned adjacent to the abutment and a shank received within the hollow body, wherein the abutment post shank is threadably received within the hollow body, wherein the abutment post head includes an internally threaded, externally accessible cavity capable of threadably receiving a screw therein.

23. An implant assembly, comprising:

an elongated hollow body including a skirt receivable within a bore provided in a bone of a patient, an internal shoulder, and an abutment extending from the skirt outwardly from the bore for supporting a prosthetic component, wherein the skirt is radially movable within the bore from a first retracted position to a second expanded position;

means for causing radial movement of the skirt from the first retracted position to the second expanded position; and an abutment post having a head positioned adjacent to the abutment and a shank received within the hollow body, wherein the abutment post includes an O-ring encircling a portion of the abutment post shank, and wherein the abutment post shank is press-fit into the hollow body.

24. An implant assembly, comprising:

an elongated hollow body including a skirt receivable within a bore provided in a bone of a patient, an internal shoulder, and an abutment extending from the skirt outwardly from the bore for supporting a prosthetic component, wherein the skirt is radially movable within the bore from a first retracted position to a second expanded position;

means for causing radial movement of the skirt from the first retracted position to the second expanded position; and an abutment post having a head positioned adjacent to the abutment and a shank received within the hollow body, wherein the abutment post head has a longitudinal axis and includes a threaded aperture therethrough having an axis inclined from the longitudinal axis, wherein the threaded aperture has an externally accessible first open end and a second open end positioned adjacent to the abutment.

25. A process for preparing a prosthesis for attachment to an abutment anchored within a bone of a patient, comprising the steps of:

associating a transfer component with the abutment;

taking an impression over the abutment with the associated transfer component;

placing a treatment crown sleeve plated with titanium nitride over the abutment;

filling the provisional prosthesis with a composite material;

placing the composite filled provisional prosthesis over the treatment crown sleeve;

inserting an implant analog having the transfer component associated therewith into the impression;

creating a stone mold utilizing the impression having the inserted implant analog; and utilizing the stone mold to form the prosthesis.

26. A process for preparing a prosthesis for attachment to an abutment anchored within a bone of a patient, comprising the steps of:

plating a portion of the abutment with a gold-colored material;

associating a transfer component with the abutment;

taking an impression over the abutment with the associated transfer component;

inserting an implant analog having the transfer component associated therewith into the impression;

creating a stone mold utilizing the impression having the inserted implant analog; and utilizing the stone mold to form the prosthesis.

27. The process of claim 26, wherein the associating, taking and inserting steps more particularly comprise the steps of:

placing a transfer sleeve over the abutment;

taking an impression wherein the transfer sleeve is transferred to the impression; and placing an implant analog into the impression through the transfer sleeve.

28. The process of claim 27, including the step of preventing rotation of the transfer sleeve relative to the abutment.

29. The process of claim 28, wherein during the step of placing the implant analog into the impression through the transfer sleeve, the transfer sleeve locks onto the implant analog in the same manner that it locks onto the abutment to prevent relative rotation thereof.

30. The process of claim 29, wherein the step of utilizing the stone mold to form the prosthesis includes the further steps of:

placing a waxing sleeve over the implant analog extending from the stone mold;

filling the waxing sleeve with a wax;

preparing a wax-up of a prosthetic component to be formed over the waxing sleeve;

removing the wax-up and the waxing sleeve from the stone mold;

investing the wax-up with the embedded waxing sleeve in a stone mold; and casting a prosthesis from the stone mold formed from the wax-up and the waxing sleeve.

31. The process of claim 30, wherein the waxing sleeve locks onto the implant analog in the same manner that the transfer sleeve locks onto the abutment.

32. The process of claim 26, wherein the associating, taking and inserting steps more particularly comprise the steps of:

attaching an impression post assembly, which comprises the transfer component, to the abutment such that a portion thereof overlies the abutment;

taking and impression over the abutment with the associated impression post assembly;

removing the impression post assembly from the abutment and attaching it in a like manner to the implant analog; and inserting the implant analog having the attached impression post assembly into the impression prior to creating the stone mold.

33. The process of claim 32, including the step of removing the impression post assembly from the implant analog prior to utilizing the stone mold to form the prosthesis.

34. The process of claim 26, wherein the prosthesis is attached to the abutment utilizing an adhesive.

35. The process of claim 26, wherein the prosthesis is mechanically attached to the abutment.

36. The process of claim 26, wherein the gold-colored material is titanium nitride.

37. The process of claim 26, wherein after the step of taking an impression over the abutment with the associated transfer component, a provisional prosthesis is secured in place over the abutment.

38. The process of claim 37, wherein the step of providing a provisional tooth includes the steps of:

placing a treatment crown sleeve over the abutment;

filling the provisional prosthesis with a composite material; and placing the composite filled provisional prosthesis over the treatment crown sleeve.

39. The process of claim 38, wherein the treatment crown sleeve is plated with titanium nitride.

40. A process for preparing a prosthesis for attachment to a bone-anchored abutment extending from a body portion of a patient, comprising the steps of:

attaching an impression post assembly to the abutment such that a portion thereof overlies the abutment;

taking an impression over the abutment with the associated impression post assembly;

removing the impression post assembly from the abutment and attaching it in a like manner to an implant analog;

inserting the implant analog having the attached impression post assembly into the impression;

creating a stone mold of the body portion of the patient surrounding the abutment utilizing the impression of the body portion of the patient surrounding the abutment having the attached impression post assembly; and removing the impression post assembly from the implant analog prior to utilizing the stone mold to form the prosthesis;

utilizing the stone mold to form the prosthesis, including the further steps of:

placing a waxing sleeve over the implant analog extending from the stone mold;

filling the waxing sleeve with a wax;

preparing a wax-up of a prosthetic component to be formed over the waxing sleeve;

removing the wax-up and the waxing sleeve from the stone mold;

investing the wax-up with the embedded waxing sleeve in a stone mold; and casting a prosthesis from the stone mold formed from the wax-up and the waxing sleeve.

41. The process of claim 40, wherein the prosthesis is attached to the abutment utilizing an adhesive.

42. The process of claim 41, wherein the prosthesis is mechanically attached to the abutment.

43. The process of claim 41, wherein, when the process is utilized to prepare a tooth prosthesis for attachment to an abutment within a mouth of the patient, after the step of removing the impression post assembly from the abutment, a provisional tooth is secured in place over the abutment including the steps of:

placing a treatment crown sleeve over the abutment;

filling a denture tooth with a composite material; and placing the composite filled denture tooth over the treatment crown sleeve.

44. A process for preparing a prosthesis for attachment to a bone-anchored abutment extending from a body portion of a patient, comprising the steps of:

placing a transfer sleeve over the abutment;

taking an impression, wherein the transfer sleeve is transferred to the impression;

placing an implant analog into the impression through the transfer sleeve;

creating a stone mold utilizing the impression having the inserted implant analog; and utilizing the stone mold to form the prosthesis, including the further steps of:

placing a waxing sleeve over the implant analog extending from the stone mold;

filling the waxing sleeve with a wax;

preparing a wax-up of a prosthetic component to be formed over the waxing sleeve;

removing the wax-up and the waxing sleeve from the stone mold;

investing the wax-up with the embedded waxing sleeve in a stone mold; and casting a prosthesis from the stone mold formed from the wax-up and the waxing sleeve.

45. The process of claim 44, including the step of preventing relative rotation of the transfer sleeve relative to the abutment, wherein during the step of placing the implant analog into the impression through the transfer sleeve, the transfer sleeve locks onto the implant analog in the same manner that it locks onto the abutment to prevent relative rotation thereof, and wherein the waxing sleeve locks onto the implant analog in the same manner that the transfer sleeve locks onto the abutment.

46. The process of claim 46, wherein the tooth prosthesis is attached to the abutment utilizing an adhesive.

47. The process of claim 46, wherein the prosthesis is mechanically matched to the abutment.

48. The process of claim 45, wherein after the step of taking an impression wherein the transfer sleeve is transferred to the impression, a provisional prosthesis is secured in place over the abutment, including the steps of placing a treatment crown sleeve over the abutment, filling the provisional prosthesis with a composite material, and placing the composite filled provisional prosthesis over the treatment crown sleeve.

49. A process for preparing a prosthesis for attachment to an abutment anchored within a bone of a patient, comprising the steps of:

placing a transfer sleeve over the abutment;

taking an impression wherein the transfer sleeve is transferred to the impression;

placing an implant analog into the impression through the transfer sleeve such that the transfer sleeve locks onto the implant analog in the same manner that it locks onto the abutment to prevent relative rotation thereof;

creating a stone mold utilizing the impression having the inserted implant analog; and utilizing the stone mold to form the prosthesis, including the further steps of:

placing a waxing sleeve over the implant analog extending from the stone mold;

filling the waxing sleeve with a wax;

preparing a wax-up of a prosthetic component to be formed over the waxing sleeve;

removing the wax-up and the waxing sleeve from the stone mold;

investing the wax-up with the embedded waxing sleeve in a stone mold; and casting a prosthesis from the stone mold formed from the wax-up and the waxing sleeve.

50. A process of claim 49, wherein the waxing sleeve locks onto the implant analog in the same manner that the transfer sleeve locks onto the abutment.

51. A process for preparing a prosthesis for attachment to an abutment anchored within a bone of a patient, comprising the steps of:

attaching an impression post assembly to the abutment such that a portion thereof overlies the abutment;

taking an impression over the abutment with the associated impression post assembly;

removing the impression post assembly from the abutment and attaching it in a like manner the implant analog;

inserting the implant analog having the attaching impression post assembly into the impression prior to creating the stone mold;

creating a stone mold utilizing the impression having the inserted implant analog; and utilizing the stone mold to form the prosthesis.

52. The process of claim 51, including the step of removing the impression post assembly from the implant analog prior to utilizing the stone mold to form the prosthesis.

53. A process for preparing a dental prosthesis, comprising the steps of:

implanting a unitary, one-piece elongated hollow body within a bore provided in a bone of patient, the elongated hollow body including a skirt receivable within the bore, and an abutment extending from the skirt outwardly from the bore for supporting the dental prosthesis;

placing a transfer sleeve over the abutment;

taken an impression, wherein the transfer sleeve is transferred to the impression;

placing and implant analog into the impression through the transfer sleeve;

creating a stone mold utilizing the impression having the inserted implant analog; and utilizing the stone mold to form the prosthesis.

54. The process of claim 53, including the step of preventing rotation of the transfer sleeve relative to the abutment.

55. The process of claim 54, wherein during the step of placing the implant analog into the impression through the transfer sleeve, the transfer sleeve locks onto the implant analog in the same manner that it locks onto the abutment to prevent relative rotation thereof.

* * * * *

UNITED STATES PATENT AND TRADEMARK OFFICE
CERTIFICATE OF CORRECTION

PATENT NO. : 6,142,782
DATED : November 7, 2000
INVENTOR(S) : Sargon Lazarof

It is certified that error appears in the above-identified patent and that said Letters Patent is hereby corrected as shown below:

Claim 46,
Line 1, delete "46" and insert -- 45 --.

Claim 47,
Line 1, delete "46" and insert -- 45 --.

Claim 48,
Line 1, delete "45" and insert -- 44 --.

Signed and Sealed this

Twenty-third Day of October, 2001

Attest:

*Attesting Officer*

NICHOLAS P. GODICI
*Acting Director of the United States Patent and Trademark Office*